(12) United States Patent
Desjarlais et al.

(10) Patent No.: US 7,610,156 B2
(45) Date of Patent: Oct. 27, 2009

(54) METHODS FOR RATIONAL PEGYLATION OF PROTEINS

(75) Inventors: John R. Desjarlais, Pasadena, CA (US); Jonathan Zalevsky, Riverside, CA (US); Gregory L. Moore, Pasadena, CA (US)

(73) Assignee: Xencor, Inc., Monrovia, CA (US)

( * ) Notice: Subject to any disclaimer, the term of this patent is extended or adjusted under 35 U.S.C. 154(b) by 271 days.

(21) Appl. No.: 10/956,352

(22) Filed: Sep. 30, 2004

(65) Prior Publication Data

US 2005/0114037 A1 May 26, 2005

Related U.S. Application Data

(63) Continuation-in-part of application No. 10/820,466, filed on Mar. 31, 2004.

(60) Provisional application No. 60/459,094, filed on Mar. 31, 2003.

(51) Int. Cl.
*G06F 19/00* (2006.01)
(52) U.S. Cl. ...................................................... 702/27
(58) Field of Classification Search .................... 702/27
See application file for complete search history.

(56) References Cited

U.S. PATENT DOCUMENTS

| | | | |
|---|---|---|---|
| 5,183,550 A | 2/1993 | Matthieson |
| 5,446,090 A | 8/1995 | Harris |
| 5,672,662 A | 9/1997 | Harris |
| 5,766,581 A | 6/1998 | Bartley |
| 5,795,569 A | 8/1998 | Bartley |
| 5,900,461 A | 5/1999 | Harris |
| 5,919,455 A | 7/1999 | Greenwald |
| 5,932,462 A | 8/1999 | Harris |
| 5,985,236 A | 11/1999 | Khan |
| 5,985,263 A | 11/1999 | Lee |
| 5,990,237 A | 11/1999 | Bentley |
| 6,113,906 A | 9/2000 | Greenwald |
| 6,188,965 B1 | 2/2001 | Mayo |
| 6,214,966 B1 | 4/2001 | Harris |
| 6,226,603 B1 | 5/2001 | Freire |
| 6,258,351 B1 | 7/2001 | Harris |
| 6,269,312 B1 | 7/2001 | Mayo |
| 6,340,742 B1 | 1/2002 | Burg |
| 6,403,312 B1 | 6/2002 | Dahiyat |
| 6,413,507 B1 | 7/2002 | Bentley |
| 6,420,339 B1 | 7/2002 | Gegg |
| 6,437,025 B1 | 8/2002 | Harris |
| 6,448,369 B1 | 9/2002 | Bentley |
| 6,461,802 B1 | 10/2002 | Van Thillo |
| 6,495,659 B2 | 12/2002 | Bentley |
| 6,708,120 B1 | 3/2004 | Mayo |
| 6,807,120 B2 | 10/2004 | Trapp |
| 7,056,695 B2 | 6/2006 | Dahiyat |
| 7,101,974 B2 | 9/2006 | Dahiyat |
| 7,231,328 B2 | 6/2007 | Desjarlais |
| 7,244,823 B2 | 7/2007 | Dahiyat |
| 7,315,786 B2 | 1/2008 | Dahiyat |
| 2002/0048772 A1 | 4/2002 | Dahiyat |
| 2002/0119492 A1 | 8/2002 | Chirino |
| 2002/0137022 A1 | 9/2002 | Li |
| 2003/0022285 A1 | 1/2003 | Chirino et al. |
| 2003/0036854 A1 | 2/2003 | Desjarlais |
| 2003/0130827 A1 | 7/2003 | Desjarlais et al. |
| 2005/0180948 A1 | 8/2005 | Desjarlais |
| 2005/0221443 A1 | 10/2005 | Desjarlais |

FOREIGN PATENT DOCUMENTS

| | | |
|---|---|---|
| EP | 0822199 A2 | 2/1998 |
| EP | 01064951 | 1/2001 |
| WO | WO 9428024 A1 | 12/1994 |
| WO | PCT/US98/07254 | 10/1998 |
| WO | WO 98/59244 A | 12/1998 |
| WO | WO 01/21823 | 3/2001 |
| WO | PCT/US01/40091 | 8/2001 |
| WO | WO 0176640 | 10/2001 |
| WO | WO 01/87925 A2 | 11/2001 |
| WO | WO 02/00165 | 1/2002 |
| WO | WO 02/25588 | 3/2002 |
| WO | WO 0249673 A2 | 6/2002 |
| WO | WO 02/073193 A | 9/2002 |

OTHER PUBLICATIONS

Ginalski et al. "Practical Lessons from Protein Structure Prediction," Nucleic Acids Research (2005) vol. 33, No. 6, pp. 1874-1891.*

Street et al., "Computational Protein Design," Structure (1999) vol. 7, No. 5, pp. R105-R108.*

(Continued)

*Primary Examiner*—Jerry Lin
(74) *Attorney, Agent, or Firm*—Morgan Lewis & Bockius LLP; Robin M. Silva, Esq.; David C. Foster, Esq.

(57) ABSTRACT

The present invention relates to the use of simulation technology to rationally optimize the locations and sizes of attached polymeric moieties for modification of therapeutic proteins and the proteins generated from this method.

16 Claims, 12 Drawing Sheets

OTHER PUBLICATIONS

U.S. Appl. No. 09/945,750, filed Aug. 31, 2001, Dahiyat.
U.S. Appl. No. 10/339,788, filed Jan. 8, 2003, Chirino.
Bailon, P. et al, (2001) "Rational design of a potent, long-lasting form of interferon: a 40-kDa-branched polyethylene glycol-conjugated interferon alpha-2a for the treatment of hepatitis C" *Bioconjug. Chem.* 12, 195-202.
Chin et al., 2003, "An Expanded Eukaryotic Genetic Code" *Science*, 301(5635): 964-7.
Chin et al., 2003, "Progress Toward an Expanded Eukaryotic Genetic Code" *Chem Biol.*10(6):511-9.
DeMaeyer et al., 1997, "All in One: A highly detailed rotamer library improves both accuracy and speed in the modelling of sidechains by dead-end elimination" *Folding and Design* 2:53-66.
Desjarlais & Berg, 1992, "Redesigning the DNA-Binding Specificty of a Zinc Finger Protein: A Data Base-Guided Approach" *Proteins* 12(2):101-4.
Desjarlais & Berg, 1993, "Use of a zinc-finger concensus sequence framework and specifity rules to design specific DNA binding proteins" *Proc Natl Acad Sci USA* 90(6):2256-60.
Desmet, et al, 2002, "Fast and Accurate Side-Chain Topology and Energy Refinement (Faster) as a New Method for Protein Structure Optimization" *Proteins*, 48:31-43.
Dunbrack & Cohen, 1997, "Bayesian statistical analysis of protein side-chain rotamer preferences" *Protein Science* 6:1661-1681.
Ewert et al., 2003, "Biophysical Properties of Human Antibody Variable Domains" *J Mol Biol* 325:531-553.
Filikov et al., 2002, "Computational stabilization of human growth hormone" *Protein Sci* 11:1452-1461.
Ginaliski et al. 2005, "Practical Lessons from Proten Structure Prediction", *Nucleic Acids Research* 33:6, 1874-1891.
Gordon & Mayo, 1999, "Branch-and-Terminate: a combinatorial optimization algorithm for protein design" *Structure Fold Des* 7:1089-98.
Henikoff & Henikoff, 1994, "Position-based Sequence Weights" *J Mol Biol* 243(4):574-8.
Henikoff & Henikoff, 2000, "Amino Acid Substitution Matrices"*Adv Protein Chem* 54:73-97.
Johnson & Wu, 2000, "Kabat Database and its applications: 30 years after the first variability plot" *Nucleic Acids Res* 28:214-218.
Johnson & Wu, 2001, "Kabat Database and its applications: future directions" *Nucleic Acids Res* 29:205-206.
Kinstler, O. et al. (2002) "Mono-N-terminal poly(ethylene glycol)-protein conjugates" *Adv. Drug Deliv. Rev.* 54. 477-485.
Kirkpatrick et al., 1983, "Optimazation by Simulated Annealing" *Science*, 220:671-680.
Lefranc et al., 1999, "IMGT, the international ImMunoGeneTics database" *Nucleic Acids Res* 27:209-212.
Kuntz, I.D. (1992) "Structure-Based Strategies for Drug Design and Discovery" *Science*, vol. 257, pp. 1078-1082.
Lefranc et al., 2001, "IMGT, the international ImMunoGeneTics database" *Nucleic Acids Res* 29:207-209.
Lefranc at al., 2003, "IMGT, the international ImMunoGeneTics database" *Nucleic Acids Res* 31:307-310.
Lehmann & Wyss, 2001, "Engineering proteins for thermostability: the use of sequence alighments versus rational design and directed evolution" *Curr Opin Biotechnol* 12(4): 371-5.
Lehmann et al., 2000, "From DNA sequence to improved functionality: using protein sequence comparisons to rapidly design a thermostable consensus phytase" *Protein Eng* 13(1):49-57.
Lehmann et al., 2000, "The consensus concept for thermostability engineering of proteins" *Biochim Biophys Acta* 1543(2):408-415.
Lovell et al., 2000, "The Penultimate Rotamer Library" *Proteins: Structure Function and Genetics* 40:389-408.
Luo et al., 2002, "Development of a cytokine analog with enhanced stability using computational ultrahigh throughput screening" *Protein Sci* 11:1218-1226.
Mendes et al., 1999, "Improved Modeling of Side-Chains In Proteins with Rotamer-Based Methods: A Flexible Rotamer Model"*Proteins: Structure, Function, and Genetics* 37:530-543.
Metropolis et al., 1953, "Equation of State Calculations by Fast Computer Machine" *J Chem Phys* 21:1087.
Morea et al., 2000, "Antibody Modeling, Implications for Engineering and Design" *Methods* 20:267-269.
Ponder & Richards, 1987, "Tertiary Templates for Proteins Use of Packing Criteria in the Enumeration of Allowed Sequences for Different Structural Classes" *J Mol Biol* 193:775-791.
Raha et al., 2000, "Prediction of Amino acid sequence from structure" *Protein Sci* 9:1106-1119.
Rath & Davidson, 2000, "The design of a hyperstable mutant of the Abp1p SH3 domain by sequence alignment analysis" *Protein Sci*, 9(12):2457-69.
Roberts, M.J. et al. (2002) "Chemistry for peptide and protein PEGylation" *Adv. Drug Deliv. Rev.* 54, 459-476.
Ruiz et al., 2000 "IMGT, the international ImMunoGeneTics database" *Nucleic Acids Re.* 28:219-221.
Simon et al., "Peptoids: A modular approach to drug discovery" *PNAS USA* 89(20):9367 (1992).
Tuffery et al., 1991, "A New Approach to the Rapid Determination of Protein Side Chain Conformations" *J Biomol Struct Dyn* 8:1267-1289.
Wang, Y.S. et al. (2002) Structural and biological characterization of PEGylated recombinant interferon alpha-2b and its therapeutic implications. *Adv. Drug Deliv.* Rev. 54, 547-570.

\* cited by examiner

METHODS FOR RATIONAL PEGYLATION OF PROTEINS

This application is a continuation-in-part of Ser. No. 10/820,466, filed Mar. 31, 2004, incorporated by reference in its entirety which claims benefit under 35 U.S.C. § 119(e) to U.S. Ser. No. 60/459,094 filed Mar. 31, 2003, which is also incorporated by reference in its entirety.

BACKGROUND OF THE INVENTION

1. Field of the Invention

The present invention relates to the use of a novel simulation technology to rationally optimize the locations and sizes of attached polymeric moieties for modification of proteins, especially therapeutic proteins.

2. Background of the Prior Art

Polymers, and particularly polyethylene glycol (PEG), are highly flexible and soluble and have gained widespread scientific and regulatory acceptance as a chemical modification for therapeutic proteins. For example, PEG attachment (PEGylation) improves PK predominantly by increasing the effective size of a protein, with most significant effects for proteins smaller than 70 kD. PEGylation can also reduce immunogenicity and aggregation. While a variety of chemistries exist for coupling PEGs of various sizes to proteins, the greatest attachment specificity generally arises from PEGylation at the N-terminus or unpaired cysteines. For further information about PEGylation, see for example Roberts, M. J. et al. (2002) "Chemistry for peptide and protein PEGylation" Adv. Drug Deliv. Rev. 54, 459-476 and Kinstler, O. et al. (2002) "Mono-N-terminal poly(ethylene glycol)-protein conjugates" Adv. Drug Deliv. Rev. 54.

Several PEGylated protein therapeutics are currently on the market or in late-stage clinical trials. Schering-Plough's PEG-Intron® (peginterferon alfa-2b) and Roche's PEGasys® (peginterferon alfa-2a), both PEGylated variants of interferon-a (IFNa) used to treat hepatitis C, show significantly improved in vivo efficacy relative to the parent molecules.

One disadvantage of many PEGylated protein therapeutics is that they have significantly reduced specific activity relative to the unmodified proteins (see for example Bailon, P. et al. (2001) "Rational design of a potent, long-lasting form of interferon: a 40-kDa-branched polyethylene glycol-conjugated interferon alpha-2a for the treatment of hepatitis C" Bioconjug. Chem. 12, 195-202; and Wang, Y. S. et al. (2002) "Structural and biological characterization of PEGylated recombinant interferon alpha-2b and its therapeutic implications" Adv. Drug Deliv. Rev. 54, 547-570). Since IFNa is a relatively small protein that contains two receptor-binding interfaces, it is not surprising that a random attachment strategy leads to a decrease in activity. Thus, although PEG attachment is generally useful for improving pharmacokinetics, it often does so at the expense of specific activity. As a result, developers of PEGylated therapeutics are often faced with the difficult challenge of seeking PEG attachment sites that minimally impact the specific activity of the modified protein.

Discovery of optimal PEGylation sites is usually accomplished empirically, requiring extensive experimentation to compare the effects of various PEGylation sites and sizes on the activity of a protein. While some attempts have been made to understand the relationship between attachment site, PEG size, and specific activity of the modified protein, such attempts have rarely yielded accurate predictions. Hence, there is a need in the field for a method that can more accurately predict the relationship among PEG attachment sites, sizes, and specific activities of the resulting proteins.

SUMMARY OF THE INVENTION

The present invention provides a method of predicting the relationship among polymer attachment sites, sizes and specific activities to generate proteins with altered properties.

It is an object of the invention to provide a computational method of designing polymer attachment sites, e.g. amino acid positions, and polymeric moieties of suitable size for attachment to different positions..

It is a further object of the invention to provide a computational method of optimizing polymer attachments to a molecule.

It is another object to produce optimized molecules with polymer attachments.

It is an additional object to provide methods of generating a set of polymeric attachment sites on a target protein comprising inputting a set of coordinates into a computer for a target protein and using a simulation module on the coordinates to create a set of amino acid positions of the protein suitable for polymeric attachment ("polymeric attachment sites"). This optionally includes generating a set of suitable polymer sizes for attachment to the polymeric attachment site(s). Optionally, the method includes experimentally generating a set of proteins with attached polymeric moieties. In some cases, as for all of the proteins outlined herein, the amino acid at the polymeric attachment site may be a non-naturally occurring amino acid such as p-acetyl-L-phenylalanine.

In a further object, the polymeric moiety for attachment is pharmaceutically acceptable, including a polyethylene glycol (PEG) molecule, including PEG derivatives, and carbohydrates, with optional ranges of from about 1000 daltons to about 100,000 daltons. The polymeric moieties may be branched or linear, and can be labile (both internally labile or labily attached).

In an additional object, the protein is a therapeutic protein and is a human erythropoeitin (EPO), a human tumor necrosis factor (TNF), a human growth hormone (hGH), a human interferon (IFN), a human granulocyte colony stimulating factor (G-CSF) and bone morphogenic protein 7 (BMP7).

In a further object, the simulation module includes MC, MD or combinations thereof.

In an additional object, the invention provides human G-CSF proteins with at least one polymeric moiety attached at at least one amino acid position selected from the group consisting of Gly5, Ala7, Ser13, Gly27, Glu34, Ala38, Lys41, His44, Glu46, Glu47, Val49, Leu50, His53, Ser54, Gly56, Trp59, Ser63, Pro66, Ser67, Ala69, Leu70, Gln71, Ala73, Glu94, Pro98, Pro102, Asp105, Thr106, Leu109, Thr116, Gln120, Glu123, Glu124, Gly126, Pro129, Ala130, Leu131, Gln132, Thr134, Gln135, Ala137, Ala140, Ala142, Ser143, Ala144, Phe145, Glu163, Arg167, and Gln174. The numbering herein is that of human G-CSF, but other molecules can be used with corresponding residues. The polymeric moieties are as described herein, with PEG, PEG derivatives and carbohydrate polymers all being specifically included.

In a further object, the invention provides HGH proteins with one or more polymeric moieties attached at one or more sites selected from the group comprising Ala155, Ser95, Thr135, Pro133, Ser57, Lys158, Asp154, Asn99, Lys140, Lys145, and Asp147. Again, the numbering herein is that of human GH, but other molecules can be used with corresponding residues.

In an additional object, the invention provides EPO proteins with one or more polymeric moieties attached at one or more sites selected from the group comprising Ala1, Ala30, Glu31, His32, Asn36, Asn38, Ala79, Ser85, Glu89, Lys116, Ile119, Asp123, Ala124, Ala125, Ala127, Ala128, Thr132, Asp136, Asp165, and Arg166. The numbering herein is that of humanEPO, but other molecules can be used with corresponding residues.

In an additional object, the invention provides TNF proteins with one or more polymeric moieties attached at one or more sites selected from the group comprising 21, 23, 31, 45, 88, 89, 111, 128 and 140. The numbering herein is that of human TNF, but other molecules can be used with corresponding residues.

BRIEF DESCRIPTION OF THE DRAWINGS

FIG. 3 shows a comparison of simulation results for PEG10000 versus PEG2000 which demonstrates that while size dramatically impacts the degrees of freedom of the attached PEG (relative to uncoupled PEG), the most optimal sites remain the same.

DETAILED DESCRIPTION OF THE INVENTION

Figure 1:
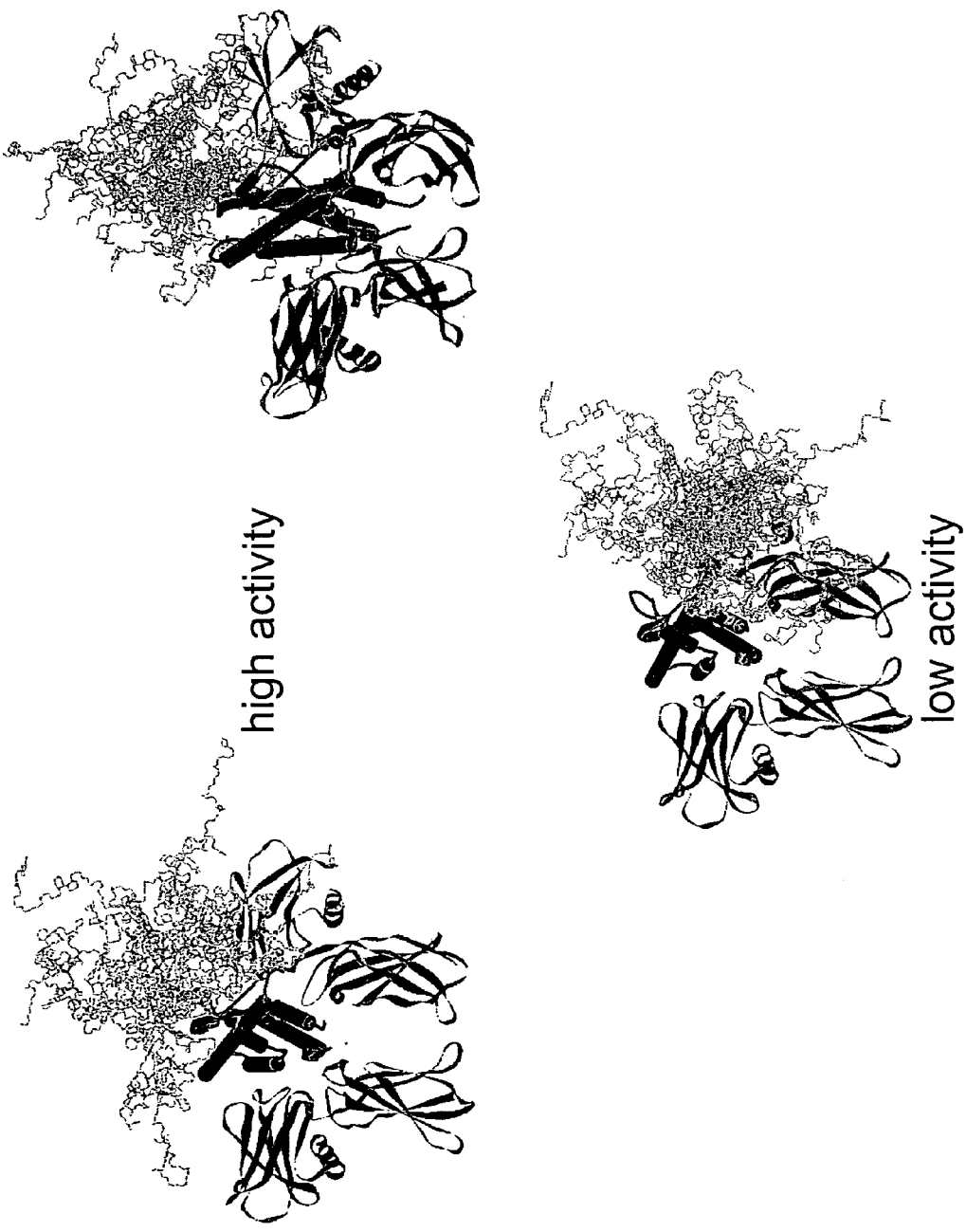
FIG. 1 is a graphic illustration depicting the range of PEG motion allowed at different attachment sites of erythropoietin (EPO). Multiple simulated conformers are shown for the PEG moiety.

The present invention provides methods for the rational design of proteins, particularly therapeutic proteins, that have polymeric moieties attached thereto. As outlined herein, the addition of polymers, particularly pharmaceutically acceptable polymers to therapeutic proteins, can result in a number of advantages, including better immunogenic profiles and increased half-life within the body. By using computer simulation models, a set of one or more amino acid positions for a particular protein can be identified that will allow polymer attachment with a minimum effect on biological activity. Similarly, these simulation models also allow the identification of preferred size ranges of polymers for particular sites. Thus, the present invention constitutes the use of molecular simulation methods to probe the range of motion of one or more attached polymeric moieties (e.g. PEG) and the dependence of this range of motion on molecular surroundings. The invention further provides statistical mechanical principles for predicting the effect of polymeric addition (e.g. PEGylation) at specific sites on a protein and its activities. As noted herein, for ease of discussion the term "PEG" is used below, but is meant to include the scope of "polymeric moiety" as defined below.

The effect of polymeric moiety attachment to a protein depends both on the site(s) of attachment and the size(s) of the polymers. The highly flexible attached PEG moiety experiences a wide range of conformations that change depending on the location of attachment and the number of monomer units in the moiety (i.e. the PEG size). The range of conformations that an attached PEG can sample depends directly on its size and its molecular surroundings. Conformations that overlap with atoms in the protein are generally prohibited due to steric clash. If the molecular surroundings change, as is the case when a PEGylated protein binds to another protein, the range of allowed conformations for the attached PEG can change dramatically. The fundamental tenets of statistical mechanics predict that this reduction of PEG conformations, known thermodynamically as a reduction of entropy, will lead to a reduced interaction affinity between the PEGylated protein and its binding partner.

As used in this invention, the term "polymer" and "polymeric moiety" or its grammatical equivalents means any non-monomeric moiety that is attachable to a protein, is at least partially soluble and has the appropriate flexibility to achieve a desired function. The polymer can be homopolymeric or heteropolymeric. In a preferred embodiment of the invention, polymer moieties may include but are not limited to alcohol such as glycols moieties and carbohydrate moieties. A preferred range of molecular weight is about 1000 Daltons to about 100,000 Daltons. The polymer may be unbranched, branched, or labile, including both internal lability, e.g. cleavage upon introduction into a patient, as well as attachment lability, wherein the linkage between the protein and the polymer is reversible The polymer may have organic or inorganic components or moieties. In a preferred embodiment, the polymer is pharmaceutically acceptable and may be attached to therapeutic proteins. A preferred example of a suitable polymer is polyethylene glycol (PEG) and its derivatives. For ease of discussion, the term "PEG" will be used, but is meant to include the scope of the term "polymer" as defined above. Examples of suitable polymers include but are not limited to, example Roberts, M. J. et al. (2002) "Chemistry for peptide and protein PEGylation" Adv. Drug Deliv. Rev. 54, 459-476 and Kinstler, O. et al. (2002) "Mono-N-terminal poly(ethylene glycol)-protein conjugates" Adv. Drug Deliv. Rev. 54; U.S. Ser. No. 60/360,722; U.S. Pat. Nos. 5,795,569;

5,766,581; EP 01064951; U.S. Pat. No. 6,340,742; WO 00176640; WO 002017; EP0822199A2; WO 0249673A2; U.S. Pat. Nos. 4,002,531; 5,183,550; 5,985,263; 5,990,237; 6,461,802; 6,495,659; 6,448,369; 6,437,025; 5,900,461; 6,413,507; 5,446,090; 5,672,662; 6,214,966; 6,258,351; 5,932,462; 5,919,455; 6,113,906; 5,985,236; WO 9428024A1; U.S. Pat. Nos. 6,340,742; 6,420,339; and WO 0187925A2, all hereby incorporated by reference. PEG derivatives can include heteroatoms and substitution groups for hydrogen atoms.

As used in this invention, the term "protein" or its grammatical equivalents is meant at least two amino acids linked together by a peptide bond. As used herein, protein includes proteins, oligopeptides and peptides. The peptidyl group may comprise naturally occurring amino acids and peptide bonds, or synthetic peptidomimetic structures, i.e. "analogs", such as peptoids (see Simon et al., PNAS USA 89(20):9367 (1992)). The amino acids may either be naturally occurring or non-naturally occurring. Preferably, any structure for which a set of rotamers is known or can be generated can be used as an amino acid. The side chains may be in either the (R) or the (S) configuration. In a preferred embodiment, the amino acids are in the (S) or L configuration. As outlined herein, particular embodiments include the use of non-naturally occurring amino acids in the proteins of the invention, particularly amino acids that facilitate the addition of polymeric moieties such as p-acetyl-L-phenylalanine. Preferred proteins are therapeutic proteins, including, but not limited to, antibodies, a human erythropoeitin (EPO), a human tumor necrosis factor (TNF), a human growth hormone (hGH), a human interferon (IFN; including alpha, beta, gamma-IFNs), a human granulocyte colony stimulating factor (G-CSF), interleukins (particularly IL-4) and bone morphogenic proteins, including BMP7.

A number of simulation methods can be used to probe the range of motion of an attached polymer moiety, including but not limited to Monte Carlo (MC) simulations and Molecular Dynamics (MD) simulations. In a preferred embodiment, MC simulations are used. At the atomic level, the range of motion of a polymer moiety such as PEG comes predominantly from rearrangements of the dihedral angles; the set of such configurations is sometimes referred to as "the rotational isomeric state model". The simple nature of the inherent flexibility of polymers such as PEG lends itself to modeling via MC simulation methods that create different polymer conformers by random generation of a set of dihedral angles describing possible chain geometries. Sampling a large number of conformers and monitoring their relationship to the molecular surroundings yields information about the allowed range of motion of the polymeric moiety. In a preferred embodiment, at least 100 polymeric configurations are randomly generated for each possible attachment site in order to assess the range of motion of the polymeric moiety in the context of the protein's different environments.

Generation of polymeric conformers can proceed in a number of different ways, including but not limited to: 1) chain buildup procedures in which each new conformer is grown from one end, sampling dihedral angles values, and defining atomic coordinates based on those angles; 2) perturbation of a starting conformer using Monte Carlo methods; and/or 3) perturbation of a starting conformer using molecular dynamics methods. Each of these (and other) methods can be performed such that one end of the conformer is placed appropriately relative to the protein of interest, or alternatively, placed relative to the protein by coordinate transformation after they have already been generated.

For the purposed of further detailing the invention, we describe the first generation method. Physically reasonable PEG (or other polymer) conformers can be generated using computer programs that generate atomic coordinates, subject to physical constraints based on the chemical nature of the repeating groups ($CH_2$—$CH_2$—O for PEG) in the polymer. In a preferred embodiment, PEG conformers are generated randomly by connecting a first atom to a pre-existing structure representing the connection moiety, and building up additional atomic coordinates from this first atom. In some embodiments, PEG conformers are generated randomly by placing a first atom at the origin, and building up additional atomic coordinates from this first atom. In preferred embodiments of the invention, the spatial relationship between two covalently connected atoms in the polymer moiety is dictated by the equilibrium bond lengths of the bonded pair, using values well-known in the art (~1.54 Å for the C—C bonds and ~1.43 Å for the C—O bonds in a PEG molecule). The angle formed between any set of three bonded atoms is dictated by the equilibrium angles of the bonded set, using values well-known in the art (~109.5 degrees for the tetrahedral geometries of the PEG atoms). The dihedral angle formed between any four covalently contiguous atoms, which is the major degree of freedom for polymeric molecules, is generally constrained to fall within one or more stable states, and is again dependent on the chemistries of the atoms involved. For modeling PEG conformers, in which the main chain atoms (alternating C and O) are $sp^3$ hybridized, the stable conformers will generally have dihedral angle values of approximately 60, 180, and 300 degrees. Hence, in a preferred embodiment, PEG or the conformers are generated in a build-up fashion using randomly selected dihedral angle values, wherein each dihedral value is close to 60, 180, or 300 degrees. In a preferred embodiment, additional small perturbations about the selected dihedral angle are included to account for inherent flexibility in the system. In a preferred embodiment, an additional constraint guides the generation of PEG conformers such that the chain is self-avoiding. That is, non-bonded atoms of the PEG moiety are not allowed to occupy the same space as other atoms. Once multiple PEG conformers of a certain size/length are generated, they are properly oriented close to any position of the target protein using coordinate transformations. In a preferred embodiment, the PEG chain and its connection moiety are attached to the protein using a rotamer library. In some embodiments, one end of the PEG conformer is oriented such that it is placed 6 Å from the protein along a vector connecting the C-alpha and centroid (the coordinate average for all side-chain atoms of the query position) coordinates of the query position.

Steric clash of individual polymer (e.g. PEG) conformers with protein atoms are monitored using a simple distance cutoff, wherein the distance between each atom in the polymeric moiety and each atom in the protein(s) is considered. For example, if any atomic pair between a PEG atom and a protein atom is closer than a user-defined cutoff distance, the PEG conformer from which that distance is derived is disallowed. In a preferred embodiment, the cutoff distance is directly proportional to the sum of the atomic radii of the atomic pair, with cutoff distances equal to one-half the sum of the atomic radii of the atomic pair being especially preferred. In some embodiments, the cutoff distance is between 0.1 and 5 Å. The fraction of sampled PEG conformers that does not clash with atoms in the protein structure (allowed conformers) indicates the range of motion allowed in that context.

It is known in the art that the efficiency of coupling of PEG moieties can depend on the location of the attachment site in the protein. Low coupling efficiencies can lead to undesirable sample heterogeneity and high production costs. In a preferred embodiment of the invention, the range of motion of an attached PEG moiety in the context of an isolated protein may be used to predict the relative coupling efficiencies at different attachment sites in the protein. These sites are also generally expected to have minimal effects on the stability of the modified protein. In general, optimal polymeration (e.g.P-EGylation) sites are those with maximal range of motion when attached.

The range of motion of an attached PEG moiety (represented quantitatively by the fraction of non-clashing PEG conformers) will change when the molecular environment of the attached PEG changes. The ratio of the ranges of motion of the attached PEG in different molecular environments relates to the effect of the attached PEG moiety on the functional activity of the protein. A common and very pertinent change in molecular environment is the binding of a cytokine to a receptor. Examples of cytokines include, but are not limited to erythropoietin, interleukin-4, G-CSF, GM-CSF, growth hormone, and the interferons. In many cases, the range of motion of an attached PEG moiety will be reduced significantly when a cytokine is bound to its receptor. Thus, in a preferred embodiment, the methods of the present invention are used to probe the range of PEG motion in two contexts: the cytokine alone, and the cytokine complexed with its receptor (s). The relative range of motion will depend on the attachment site and size of the PEG moiety. Simulations are performed independently for each amino acid position of the cytokine. In a preferred embodiment, amino acid positions with the smallest reduction of PEG motion upon binding are considered to be the most optimal attachment sites. Attachment of PEG at these sites is predicted to have the smallest effect on the binding affinity—and signaling activity—between cytokine and receptor.

In a preferred embodiment of the invention, the predicted coupling efficiency, predicted effect on protein stability, and the predicted effect on activity are all used to guide the choice of optimal PEGylation sites. In a preferred embodiment of the invention, those sites for which greater than 20% of simulated PEG2000 chains are non-clashing in the free state are considered optimal sites for attachment. In additional preferred embodiments, sites with high predicted coupling efficiency are further screened to identify those that retain PEG range of motion upon receptor binding. In a preferred embodiment, high coupling efficiency sites for which greater than 20% of simulated PEG2000 chains are non-clashing in the bound state are considered optimal for retention of activity. In an especially preferred embodiment, high coupling efficiency sites for which greater than 30% of simulated PEG2000 chains are non-clashing in the bound state are considered especially optimal for retention of activity. Although the magnitudes of the predicted coupling efficiency, predicted effect on protein stability, and the predicted effect on activity depend directly on PEG size, the rank order of preferred PEGylation sites does not (see FIG. 3, Example 1). Independence from PEG size indicates that preferred sites will also be ideal for attachment of any polymer moiety with a high degree of flexibility (e.g. a carbohydrate). In additional preferred embodiments, other considerations are also incorporated, including but not limited to the use of computational techniques to assess the compatibility of amino acid changes and PEG attachment chemistries with the structure and function of the protein.

Computational techniques can generate rational solutions to design problems such as identifying optimal PEGylation sites on proteins. These techniques may be used to identify preferred sites for PEGylation without the need for extensive empirical experimentation.

A range of PEG sizes may be attached to proteins using a variety of chemistries. Linkages are typically formed between PEG and primary amines (lysine side chains or the protein N-terminus), thiols (cysteine residues), or histidines. Linkages can also be formed between PEG and nonnatural amino acids, especially those involving an acetyl moiety, for instance, p-acetyl-L-phenylalanine. Lysine occurs frequently on the surface of proteins, so PEGylation of lysine side chains generally produces a mix of PEGylation products. Since the pKa of the N-terminus is significantly different than the pKa of a typical lysine side chain, it is possible to specifically target the N-terminus for modification. However, in some embodiments, PEGylation at the N-terminus is not preferred. Similarly, as most proteins contain very few free cysteine residues, cysteines (naturally occurring or engineered) are commonly targeted for site-specific PEGylation. That is, In a preferred embodiment the present invention finds use for designing optimal cysteine incorporation sites for site-specific PEGylation. In some cases, this involves running the simulation module of the invention to identify a suitable PEG site, and then creating a protein with a cysteine substitution at that residue position. In alternative preferred embodiments, the present invention finds use for replacing specific lysine or histidine residues with alternative amino acids, such that PEGylation at such residues is no longer possible. The choice of which lysines or histidines to remove depends on the extent to which the simulations predict that their PEGylation will interfere with the function of the protein. In alternative preferred embodiments, the present invention finds use for designing optimal incorporation sites for nonnatural amino acids, especially p-acetyl-L-phenylalanine, for site-specific PEGylation. The set of optimal incorporation sites identified from simulation is not strongly dependent on attachment chemistry (see Example 7, FIGS. 10 and 11). Independence from attachment chemistry indicates that preferred sites would be ideal for attachment of any polymer moiety with a high degree of flexibility (e.g., carbohydrate).

In some embodiments, it is desirable to use reversible (labile) PEGylation to temporarily inactivate a protein while improving its half-life in vivo. This concept can be used, for example, to generate a slow-release version of a therapeutic protein or a protein that bypasses some biological systems at early time points after administration. The linkage between the PEG moieties described herein and the therapeutic protein are preferably covalent and optionally but preferably reversible. That is, under physiological conditions, the linkage between the PEG and the protein is preferably labile. Using reversible chemistry for PEG attachment allows regeneration of active therapeutic protein over time, preferably following absorption from the site of administration. For such situations, the present invention finds use for the optimization of reversible PEG attachment sites. In some cases it is desirably that biological activity is lost when the PEG is attached; in other cases, the activity is stable or even increased.

In a preferred embodiment of the invention, MC or MD simulations are used to probe the range of motion of additional polymer moieties, including but not limited to carbohydrate moieties such as dextrans. In an alternative embodiment, MC simulations of PEG moieties are used as a proxy to predict the effects of attachment of any flexible moiety on the function of a protein.

Attachment of a polymeric moiety to a protein can proceed using a variety of coupling chemistries. Because these chemistries involve molecular entities of various shapes and sizes, additional consideration of attachment sites will include an assessment of the compatibility of such entities with the atomic structure of the target protein. For example, one of the most commonly used chemistries for PEG attachment is to couple a PEG-maleimide to free thiol groups on the protein (e.g. unpaired cysteine residues) to form a disulfide link between the protein cysteine and the PEG moiety. This attachment constitutes a significant change in atomic structure in the vicinity of the attachment site. In some cases, the shape and size of the attachment group will not be compatible with the local atomic environment at the attachment site. Such incompatibility will potentially affect the efficiency of coupling, the structure of the protein, the function of the protein, and/or the stability of the protein.

The compatibility of a PEG attachment chemistry with individual sites on a protein can be assessed using computational screening methods. Computational screening, viewed broadly, has four steps: 1) selection and preparation of the protein template structure or structures, 2) selection of variable positions, amino acids to be considered at those positions, and/or selection of rotamers to model considered amino acids, 3) energy calculation, and 4) combinatorial optimization. In more detail, the process of computational screening can be described as follows. A three-dimensional template structure of a protein is used as the starting point. The positions to be optimized are identified, which may be the entire protein sequence or subset(s) thereof. Amino acids (including amino acids with attached coupling groups) that will be considered at each position are selected. In a preferred embodiment, each considered amino acid may be represented by a discrete set of allowed conformations, called rotamers. Interaction energies are calculated between each considered amino acid and each other considered amino acid, and the rest of the protein, including the protein backbone and invariable residues. In a preferred embodiment, interaction energies are calculated between each considered amino acid side chain rotamer and each other considered amino acid side chain rotamer and the rest of the protein, including the protein backbone and invariable residues. One or more combinatorial search algorithms are then used to identify the lowest energy sequence and/or low energy sequences or lowest energy rotamer states. In order to optimize the selection of PEG attachment sites, this process is repeated for a number of variable positions. Positions for which modeling of the PEG attachment chemistry yields a favorable calculated energy are generally preferred attachment sites. In additional embodiments, compensatory mutations at non-attachment PEG sites can be made to optimize the structural fit of the attachment group at the attachment site.

In a preferred embodiment, Protein Design Automation® (PDA®) technology is used. See, for example, U.S. Pat. Nos. 6,188,965; 6,269,312; 6,403,312; 6,708,120; U.S. Ser. Nos. 09/782,004; 09/927,790; 10/218,102; PCT WO 98/07254; PCT WO 01/40091; and PCT WO 02/25588. In another preferred embodiment, a computational screening method substantially similar to Sequence Prediction Algorithm™ (SPA™) technology is used, as is described in (Raha et al., 2000, Protein Sci 9:1106-1119), U.S. Ser. Nos. 09/877,695, and 10/071,859. In some embodiments, combinations of different computational screening methods are used, including combinations of PDA® technology and SPA™ technology, as well as combinations of these computational methods in combination with other design tools. Similarly, these computational methods can be used simultaneously or sequentially, in any order.

A template structure is used as input into the computational screening calculations. By "template structure" herein is meant the structural coordinates of part or all of a protein to be optimized. The template structure may be any protein for which a three dimensional structure (that is, three dimensional coordinates for a set of the protein's atoms) is known or may be calculated, estimated, modeled, generated, or determined. The three dimensional structures of proteins may be determined using methods including but not limited to X-ray crystallographic techniques, nuclear magnetic resonance (NMR) techniques, de novo modeling, and homology modeling. If optimization is desired for a protein for which the structure has not been solved experimentally, a suitable structural model may be generated that may serve as the template for computational screening calculations. Methods for generating homology models of proteins are known in the art, and these methods find use in the present invention. See for example, Luo, et al. 2002, Protein Sci 11: 1218-1226, Lehmann & Wyss, 2001, Curr Opin Biotechnol 12(4):371-5.; Lehmann et al., 2000, Biochim Biophys Acta 1543(2):408-415; Rath & Davidson, 2000, Protein Sci, 9(12):2457-69; Lehmann et al., 2000, Protein Eng 13(1):49-57; Desjarlais & Berg, 1993, Proc Natl Acad Sci USA 90(6):2256-60; Desjarlais & Berg, 1992, Proteins 12(2):101-4; Henikoff & Henikoff, 2000, Adv Protein Chem 54:73-97; Henikoff & Henikoff, 1994, J Mol Biol 243(4):574-8; Morea et al., 2000, Methods 20:267-269. Protein/protein complexes may also be obtained using docking methods. Suitable protein structures that may serve as template structures include, but are not limited to, all of those found in the Protein Data Base compiled and serviced by the Research Collaboratory for Structural Bioinformatics (RCSB, formerly the Brookhaven National Lab).

The template structure may be of a protein that occurs naturally or is engineered. The template structure may be of a protein that is substantially encoded by a protein from any organism, with human, mouse, rat, rabbit, and monkey preferred. The template structure may comprise any of a number of protein structural forms. The template structure protein may be glycosylated or unglycosylated. The template structure may comprise more than one protein chain. The template structure may additionally contain nonprotein components, including but not limited to small molecules, substrates, cofactors, metals, water molecules, prosthetic groups, polymers and carbohydrates. In a preferred embodiment, the template structure is a plurality or set of template proteins, for example an ensemble of structures such as those obtained from NMR. Alternatively, the set of template structures is generated from a set of related proteins or structures, or artificially created ensembles. The composition and source of the template structure depends on the engineering goal.

The template structure may be modified or altered prior to design calculations. A variety of methods for template structure preparation are described in U.S. Pat. Nos. 6,188,965; 6,269,312; 6,403,312; 6,807,120; U.S. Ser. Nos. 09/782,004; 09/927,790; 09/877,695; 10/071,859, 10/218,102; PCT WO 98/07254; PCT WO 01/40091; and PCT WO 02/25588. For example, in a preferred embodiment, explicit hydrogens may be added if not included within the structure. In an alternate embodiment, energy minimization of the structure is run to relax strain, including strain due to van der Waals clashes, unfavorable bond angles, and unfavorable bond lengths. Alternatively, the template structure is altered using other methods, such as manually, including directed or random perturbations. It is also possible to modify the template structure during later steps of computational screening, including during the energy calculation and combinatorial optimization steps. In an alternate embodiment, the template structure is not modified before or during computational screening calculations.

As will be appreciated by those in the art, there are a variety of computational analyses which can be run. The first is the identification of amino acid positions for polymeric moiety attachment ("polymer sites"). Secondly, additional computational analyses can be done to alter the amino acids at additional positions (e.g. variable positions as discussed below). That is, in some cases, a protein can be optimized or altered with amino acid substitutions as compared to the wild type protein prior to or simultaneously with the identification of suitable polymer attachment sites and suitable polymers and/or polymer sizes.

Once a template structure has been obtained, variable positions are chosen. By "variable position" herein is meant a position at which the amino acid identity is allowed to be altered in a computational screening calculation. As is known in the art, allowing amino acid modifications to be considered only at certain variable positions reduces the complexity of a calculation and enables computational screening to be more directly tailored for the design goal. One or more residues may be variable positions in computational screening calculations. Positions that are chosen as variable positions may be those that contribute to or are hypothesized to contribute to the protein property to be optimized. Residues at variable positions may contribute favorably or unfavorably to a specific protein property. For example, a residue that has an exposed hydrophobic side chain may be responsible for causing unfavorable aggregation, and thus this position may be varied in design calculations aimed at improving solubility. Variable positions may be those positions that are directly involved in interactions that are determinants of a particular protein property. By "contact" herein is meant some chemical interaction between at least one atom of a protein residue with at least one atom of the bound protein receptor, with chemical interaction including, but not limited to van der Waals interactions, hydrogen bond interactions, electrostatic interactions, and hydrophobic interactions. In an alternative embodiment, variable positions may include those positions that are indirectly involved in a protein property, i.e. such positions may be proximal to residues that are known to or hypothesized to contribute to a protein property. For example, the binding site of a protein may be defined to include all residues within a certain distance, for example 4-10 Å, of any residue that is in van der Waals contact with a corresponding receptor. Thus variable positions in this case may be chosen not only as residues that directly contact a receptor, but also those that contact residues that contact a receptor and thus influence binding indirectly. The specific positions chosen are dependent on the design strategy being employed.

One or more positions in the template structure that are not variable may be floated. By "floated position" herein is meant a position at which the amino acid conformation but not the amino acid identity is allowed to vary in a computational screening calculation. In one embodiment, the floated position may have the parent amino acid identity. For example, floated positions may be positions that are within a small distance, for example 5 Å, of a variable position residue. In an alternate embodiment, a floated position may have a non-parent amino acid identity. Such an embodiment may find use in the present invention, for example, when the goal is to evaluate the energetic or structural outcome of a specific mutation.

Positions that are not variable or floated are fixed. By "fixed position" herein is meant a position at which the amino acid identity and the conformation are held constant in a computational screening calculation. Positions that may be fixed include residues that are not known to be or hypothesized to be involved in the property to be optimized. In this case the assumption is that there is little or nothing to be gained by varying these positions. Positions that are fixed may also include positions whose residues are known or hypothesized to be important for maintaining proper folding, structure, stability, solubility, and/or biological function. For example, positions may be fixed for residues that interact with a particular receptor or residues that encode a glycosylation site in order to ensure that binding to the receptor and proper glycosylation respectively are not perturbed. Likewise, if stability is being optimized, it may be beneficial to fix positions that directly or indirectly interact with a receptor. Fixed positions may also include structurally important residues such as cysteines participating in disulfide bridges, residues critical for determining backbone conformation such as proline or glycine, critical hydrogen bonding residues, and residues that form favorable packing interactions.

The next step in computational screening is to select a set of possible amino acid identities that will be considered at each particular variable position. This set of possible amino acids is herein referred to as "considered amino acids" at a variable position. "Amino acids" as used herein refers to the set of 20 natural amino acids, any nonnatural or synthetic analogues thereof, and any other amino acid of interest. In one embodiment, all 20 natural amino acids are considered. Alternatively, a subset of amino acids, or even only one amino acid is considered at a given variable position. As will be appreciated by those skilled in the art, there is a computational benefit to considering only certain amino acid identities at variable positions, as it decreases the combinatorial complexity of the search. Furthermore, considering only certain amino acids at variable positions may be used to tailor calculations toward specific design strategies. For example, for solubility optimization, it may be beneficial to allow only polar amino acids to be considered at residues that are exposed to solvent in the absence of carbohydrate. Nonnatural amino acids, including synthetic amino acids and analogues of natural amino acids, may also be considered amino acids. For example see Chin et al., 2003, Science, 301(5635): 964-7; and Chin et al., 2003, Chem Biol.10(6):511-9.

A wide variety of methods may be used, alone or in combination, to select which amino acids will be considered at each position. For example, the set of considered amino acids at a given variable position may be chosen based on the degree of exposure to solvent. Hydrophobic or nonpolar amino acids typically reside in the interior or core of a protein, which are inaccessible or nearly inaccessible to solvent. Thus at variable core positions it may be beneficial to consider only or mostly nonpolar amino acids such as alanine, valine, isoleucine, leucine, phenylalanine, tyrosine, tryptophan, and methionine. Hydrophilic or polar amino acids typically reside on the exterior or surface of proteins, which have a significant degree of solvent accessibility. Thus at variable surface positions it may be beneficial to consider only or mostly polar amino acids such as alanine, serine, threonine, aspartic acid, asparagine, glutamine, glutamic acid, arginine, lysine, tyrosine, and histidine. Some positions are partly exposed and partly buried, and are not clearly protein core or surface positions, in a sense serving as boundary residues between core and surface residues. Thus at such variable boundary positions it may be beneficial to consider both nonpolar and polar amino acids. Determination of the degree of solvent exposure at variable positions may be by subjective evaluation or visual inspection of the template structure by one skilled in the art of protein structural biology, or by using a variety of algorithms that are known in the art. Selection of amino acid types to be considered at variable positions may be aided or determined wholly by computational methods, such as calculation of solvent accessible surface area, or using algorithms that assess orientation relative to a solvent accessible surface, as outlined in U.S. Pat. Nos. 6,188,965; 6,269,312; 6,403,312; 6,708,120; U.S. Ser. Nos. 09/782,004; 09/927,790; 10/218,102; PCT WO 98/07254; PCT WO 01/40091; and PCT WO 02/25588. In one embodiment, each variable position may be classified explicitly as a core, surface, or boundary position or a classification substantially similar to core, surface, or boundary.

In an alternate embodiment, selection of the set of amino acids allowed at variable positions may be hypothesis-driven. Hypotheses for which amino acid types should be considered at variable positions may be derived by a subjective evaluation or visual inspection of the template structure by one skilled in the art of protein structural biology. For example, if it is suspected that a hydrogen bonding interaction may be favorable at a variable position, polar residues that have the capacity to form hydrogen bonds may be considered, even if the position is in the core. Likewise, if it is suspected that a hydrophobic packing interaction may be favorable at a variable position, nonpolar residues that have the capacity to form favorable packing interactions may be considered, even if the position is on the surface. Other examples of hypothesis-driven approaches may involve issues of backbone flexibility or protein fold. As is known in the art, certain residues, for example proline, glycine, and cysteine, play important roles in protein structure and stability. Glycine enables greater backbone flexibility than all other amino acids, proline constrains the backbone more than all other amino acids, and cysteines may form disulfide bonds. It may therefore be beneficial to include one or more of these amino acid types to achieve a desired design goal. Alternatively, it may be beneficial to exclude one or more of these amino acid types from the list of considered amino acids.

In an alternate embodiment, subsets of amino acids may be chosen to maximize coverage. In this case, additional amino acids with properties similar to that in the template structure may be considered at variable positions. For example, if the residue at a variable position in the template structure is a large hydrophobic residue, additional large hydrophobic amino acids may be considered at that position. Alternatively, subsets of amino acids may be chosen to maximize diversity. In this case, amino acids with properties dissimilar to those in the template structure may be considered at variable positions. For example, if the residue at a variable position in the template is a large hydrophobic residue, amino acids that are small, polar, etc. may be considered.

As is known in the art, some computational screening methods require only the identity of considered amino acids to be determined during design calculations. That is, no information is required concerning the conformations or possible conformations of the amino acid side chains. Other preferred methods utilize a set of discrete side chain conformations, called rotamers, which are considered for each amino acid. Thus, a set of rotamers may be considered at each variable and floated position. Rotamers may be obtained from published rotamer libraries (see for example, Lovel et al., 2000, Proteins: Structure Function and Genetics 40:389-408; Dunbrack & Cohen, 1997, Protein Science 6:1661-1681; DeMaeyer et al., 1997, Folding and Design 2:53-66; Tuffery et al., 1991, J Biomol Struct Dyn 8:1267-1289, Ponder & Richards, 1987, J Mol Biol 193:775-791), or generated by analysis of protein structures. As is known in the art, rotamer libraries may be backbone-independent or backbone-dependent. Rotamers may also be obtained from molecular mechanics or ab initio calculations, and using other methods. Rotamer states may also be obtained by applying geometric constraints consistent with the atomic connectivity and hybridization states of the atomic constituents. These methods are particularly applicable for generating rotamer states for non-natural amino acids, including functional groups (e.g. maleimide) used for PEG attachment. In a preferred embodiment, a flexible rotamer model is used (see Mendes et al., 1999, Proteins: Structure, Function, and Genetics 37:530-543). Similarly, artificially generated rotamers may be used, or augment the set chosen for each amino acid and/or variable position. In one embodiment, at least one conformation that is not low in energy is included in the list of rotamers. In an alternate embodiment, the rotamer of the variable position residue in the template structure is included in the list of rotamers allowed for that variable position. In an alternate embodiment, only the identity of each amino acid considered at variable positions is provided, and no specific conformational states of each amino acid are used during design calculations. That is, use of rotamers is not essential for computational screening.

Experimental information may be used to guide the choice of variable positions and/or the choice of considered amino acids at variable positions. As is known in the art, mutagenesis experiments are often carried out to determine the role of certain residues in protein structure and function, for example, which protein residues play a role in determining stability, or which residues make up the interface of a protein-protein interaction. Data obtained from such experiments are useful in the present invention. For example, variable positions for affinity enhancement could involve varying all positions at which mutation has been shown to affect binding. Similarly, the results from such an experiment may be used to guide the choice of allowed amino acid types at variable positions. For example, if certain types of amino acid substitutions are found to be favorable, similar types of those amino acids may be considered. In one embodiment, additional amino acids with properties similar to those that were found to be favorable experimentally may be considered at variable positions. For example, if experimental mutation of a variable position at an protein-receptor interface to a large hydrophobic residue was found to be favorable, the user may choose to include additional large hydrophobic amino acids at that position in the computational screen. As is known in the art, display and other selection technologies may be coupled with random mutagenesis to generate a list or lists of amino acid substitutions that are favorable for the selected property. Such a list or lists obtained from such experimental work find use in the present invention. For example, positions that are found to be invariable in such an experiment may be excluded as variable positions in computational screening calculations, whereas positions that are found to be more acceptable to mutation or respond favorably to mutation may be chosen as variable positions. Similarly, the results from such experiments may be used to guide the choice of allowed amino acid types at variable positions. For example, if certain types of amino acids arise more frequently in an experimental selection, similar types of those amino acids may be considered. In one embodiment, additional amino acids with properties similar to those that were found to be favorable experimentally may be considered at variable positions. For example, if selected mutations at a variable position that resides at an protein-receptor interface are found to be uncharged polar amino acids, the user may choose to include additional uncharged or charged polar amino acids at that position.

Sequence information may also be used to guide choice of variable positions and/or the choice of amino acids considered at variable positions. As is known in the art, some proteins share a common structural scaffold and are homologous in sequence. This information may be used to gain insight into particular positions in the protein family. As is known in the art, sequence alignments are often carried out to determine which protein residues are conserved and which are not conserved. That is to say, by comparing and contrasting alignments of protein sequences, the degree of variability at a position may be observed, and the types of amino acids that occur naturally at positions may be observed. Data obtained from such analyses are useful in the present invention. The benefit of using sequence information to choose variable positions and considered amino acids at variable positions are several fold. For choice of variable positions, the primary advantage of using sequence information is that insight may be gained into which positions are more tolerant and which are less tolerant to mutation. Thus sequence information may aid in ensuring that quality diversity, i.e. mutations that are not deleterious to protein structure, stability, etc., is sampled computationally. The same advantage applies to use of sequence information to select amino acid types considered at variable positions. That is, the set of amino acids that occur in a protein sequence alignment may be thought of as being pre-screened by evolution to have a higher chance than random for being compatible with a protein's structure, stability, solubility, function, etc. Thus higher quality diversity is sampled computationally. A second benefit of using sequence information to select amino acid types considered at variable positions is that certain alignments may represent sequences that may be less immunogenic than random sequences. For example, if the amino acids considered at a given variable position are the set of amino acids which occur at that position in an alignment of human protein sequences, those amino acids may be thought of as being pre-screened by nature for generating no or low immune response if the optimized protein is used as a human therapeutic.

The source of the sequences may vary widely, and include one or more of the known databases, including but not limited to the Kabat database (Johnson & Wu, 2001, Nucleic Acids Res 29:205-206; Johnson & Wu, 2000, Nucleic Acids Res 28:214-218), the IMGT database (IMGT, the international ImMunoGeneTics information system®; Lefranc et al., 1999, Nucleic Acids Res 27:209-212; Ruiz et al., 2000 Nucleic Acids Re. 28:219-221; Lefranc et al., 2001, Nucleic Acids Res 29:207-209; Lefranc et al., 2003, Nucleic Acids Res 31:307-310), and VBASE, SwissProt, GenBank and Entrez, and EMBL Nucleotide Sequence Database. Protein sequence information can be obtained, compiled, and/or generated from sequence alignments of naturally occurring proteins from any organism, including but not limited to mammals. Protein sequence information can be obtained from a database that is compiled privately. There are numerous sequence-based alignment programs and methods known in the art, and all of these find use in the present invention for generation of sequence alignments of proteins.

Once alignments are made, sequence information can be used to guide choice of variable positions. Such sequence information can relate the variability, natural or otherwise, of a given position. Variability herein should be distinguished from variable position. Variability refers to the degree to which a given position in a sequence alignment shows variation in the types of amino acids that occur there. Variable position, to reiterate, is a position chosen by the user to vary in amino acid identity during a computational screening calculation. Variability may be determined qualitatively by one skilled in the art of bioinformatics. There are also methods known in the art to quantitatively determine variability that may find use in the present invention. The most preferred embodiment measures Information Entropy or Shannon Entropy. Variable positions can be chosen based on sequence information obtained from closely related protein sequences, or sequences that are less closely related.

The use of sequence information to choose variable positions finds broad use in the present invention. For example, if an interface position in the template structure is tryptophan, and tryptophan is observed at that position in greater than 90% of the sequences in an alignment, it may be beneficial to leave that position fixed. In contrast, if another interface position is found to have a greater level of variability, for example if five different amino acids are observed at that position with frequencies of approximately 20% each, that position may be chosen as a variable position. In another embodiment, visual inspection of aligned protein sequences may substitute for or aid visual inspection of a protein structure. Sequence information can also be used to guide the choice of amino acids considered at variable positions. Such sequence information can relate to how frequently an amino acid, amino acids, or amino acid types (for example polar or nonpolar, charged or uncharged) occur, naturally or otherwise, at a given position. In one embodiment, the set of amino acids considered at a variable position may comprise the set of amino acids that is observed at that position in the alignment. Thus, the position-specific alignment information is used directly to generate the list of considered amino acids at a variable position in a computational screening calculation. Such a strategy is well known in the art; see for example Lehmann & Wyss, 2001, Curr Opin Biotechnol 12(4): 371-5; Lehmann et al., 2000, Biochim Biophys Acta 1543(2):408-415; Rath & Davidson, 2000, Protein Sci, 9(12):2457-69; Lehmann et al., 2000, Protein Eng 13(1):49-57; Desjarlais & Berg, 1993, Proc Natl Acad Sci USA 90(6):2256-60; Desjarlais & Berg, 1992, Proteins 12(2):101-4; Henikoff & Henikoff, 2000, Adv Protein Chem 54:73-97; Henikoff & Henikoff, 1994, J Mol Biol 243(4):574-8. In an alternate embodiment, the set of amino acids considered at a variable position or positions may comprise a set of amino acids that is observed most frequently in the alignment. Thus, a certain criteria is applied to determine whether the frequency of an amino acid or amino acid type warrants its inclusion in the set of amino acids that are considered at a variable position. As is known in the art, sequence alignments may be analyzed using statistical methods to calculate the sequence diversity at any position in the alignment and the occurrence frequency or probability of each amino acid at a position. Such data may then be used to determine which amino acids types to consider. In the simplest embodiment, these occurrence frequencies are calculated by counting the number of times an amino acid is observed at an alignment position, then dividing by the total number of sequences in the alignment. In other embodiments, the contribution of each sequence, position or amino acid to the counting procedure is weighted by a variety of possible mechanisms. In a preferred embodiment, the contribution of each aligned sequence to the frequency statistics is weighted according to its diversity weighting relative to other sequences in the alignment. A common strategy for accomplishing this is the sequence weighting system recommended by Henikoff and Henikoff (Henikoff & Henikoff, 2000, Adv Protein Chem 54:73-97; Henikoff & Henikoff, 1994, J Mol Biol 243:574-8. In a preferred embodiment, the contribution of each sequence to the statistics is dependent on its extent of similarity to the target sequence, i.e. the template structure used, such that sequences with higher similarity to the target sequence are weighted more highly. Examples of similarity measures include, but are not limited to, sequence identity, BLOSUM similarity score, PAM matrix similarity score, and BLAST score. In an alternate embodiment, the contribution of each sequence to the statistics is dependent on its known physical or functional properties. These properties include, but are not limited to, thermal and chemical stability, contribution to activity, and solubility. For example, when optimizing protein for solubility, those sequences in an alignment that are known to be most soluble (for example see Ewert et al., 2003, J Mol Biol 325:531-553), will contribute more heavily to the calculated frequencies.

In one embodiment, sequence alignment information is combined with energy calculation, as discussed below. For example, pseudo energies can be derived from sequence information to generate a scoring function. The use of a sequence-based scoring function may assist in significantly reducing the complexity of a calculation. However, as is appreciated by those skilled in the art, the use of a sequence-based scoring function alone may be inadequate because sequence information can often indicate misleading correlations between mutations that may in reality be structurally conflicting. Thus, in a preferred embodiment, a structure-based method of energy calculation is used, either alone or in combination with a sequence-based scoring function. That is, preferred embodiments do not rely on sequence alignment information alone as the analysis step.

Energy calculation refers to the process by which amino acid modifications are scored. The energies of interaction are measured by one or more scoring functions. A variety of scoring functions find use in the present invention for calculating energies. Scoring functions may include any number of potentials, herein referred to as the energy terms of a scoring function, including but not limited to a van der Waals potential, a hydrogen bond potential, an atomic solvation potential or other solvation models, a secondary structure propensity potential, an electrostatic potential, a torsional potential, and an entropy potential. At least one energy term is used to score each variable or floated position, although the energy terms may differ depending on the position, considered amino acids, and other considerations. In one embodiment, a scoring function using one energy term is used. In the most preferred embodiment, energies are calculated using a scoring function that contains more than one energy term, for example describing van der Waals, salvation, electrostatic, and hydrogen bond interactions, and combinations thereof. In additional embodiments, additional energy terms include but are not limited to entropic terms, torsional energies, and knowledge-based energies.

A variety of scoring functions are described in U.S. Pat. Nos. 6,188,965; 6,269,312; 6,403,312; U.S. Ser. Nos. 09/782, 004; 09/927,790; 09/877,695; 10/071,859, 10/218,102; PCT WO 98/07254; PCT WO 01/40091; and PCT WO 02/25588. As will be appreciated by those skilled in the art, scoring functions need not be limited to physico-chemical energy terms. For example, knowledge-based potentials may find use in the computational screening methodology of the present invention. Such knowledge-based potentials may be derived from protein sequence and/or structure statistics including but not limited to threading potentials, reference energies, pseudo energies, homology-based energies, and sequence biases derived from sequence alignments. In a preferred embodiment, a scoring function is modified to include models for immunogenicity, such as functions derived from data on binding of peptides to MHC (Major Histocompatability Complex), that may be used to identify potentially immunogenic sequences (see for example U.S. Ser. Nos. 09/903,378; 10/039,170; 60/222,697; 10/339788; PCT WO 01/21823; and PCT WO 02/00165). In one embodiment, sequence alignment information can be used to score amino acid substitutions. For example, comparison of protein sequences, regardless of whether the source of said proteins is human, monkey, mouse, or otherwise, may be used to suggest or score amino acid mutations in the computational screening methodology of the present invention. In one embodiment, as is known in the art, one or more scoring functions may be optimized or "trained" during the computational analysis, and then the analysis re-run using the optimized system. Such altered scoring functions may be obtained for example, by training a scoring function using experimental data. As will be appreciated by those skilled in the art, a number of force fields, which are comprised of one or more energy terms, may serve as scoring functions. Force fields include but are not limited to ab initio or quantum mechanical force fields, semi-empirical force fields, and molecular mechanics force fields. Scoring functions that are knowledge-based or that use statistical methods may find use in the present invention. These methods may be used to assess the match between a sequence and a three-dimensional protein structure, and hence may be used to score amino acid substitutions for fidelity to the protein structure. In one embodiment, molecular dynamics calculations may be used to computationally screen sequences by individually calculating mutant sequence scores.

There are a variety of ways to represent amino acids in order to enable efficient energy calculation. In a preferred embodiment, considered amino acids are represented as rotamers, as described previously, and the energy (or score) of interaction of each possible rotamer at each variable and floated position with the other variable and floated rotamers, with fixed position residues, and with the backbone structure and any non-protein atoms, is calculated. In a preferred embodiment, two sets of interaction energies are calculated for each side chain rotamer at every variable and floated position: the interaction energy between the rotamer and the fixed atoms (the "singles" energy), and the interaction energy between the variable and floated positions rotamer and all other possible rotamers at every other variable and floated position (the "doubles" energy). In an alternate embodiment, singles and doubles energies are calculated for fixed positions as well as for variable and floated positions. In an alternate embodiment, considered amino acids are not represented as rotamers.

An important component of computational screening is the identification of one or more sequences that have a favorable score, i.e. are low in energy. Determining a set of low energy sequences from an extremely large number of possibilities is nontrivial, and to solve this problem a combinatorial optimization algorithm is employed. The need for a combinatorial optimization algorithm is illustrated by examining the number of possibilities that are considered in a typical computational screening calculation. The discrete nature of rotamer sets allows a simple calculation of the number of possible rotameric sequences for a given design problem. A backbone of length n with m possible rotamers per position will have $m^n$ possible rotamer sequences, a number that grows exponentially with sequence length. For very simple calculations, it is possible to examine each possible sequence in order to identify the optimal sequence and/or one or more favorable sequences. However, for a typical design problem, the number of possible sequences (up to $10^{80}$ or more) is sufficiently large that examination of each possible sequence is intractable. A variety of combinatorial optimization algorithms may then be used to identify the optimum sequence and/or one or more favorable sequences. Combinatorial optimization algorithms may be divided into two classes: (1) those that are guaranteed to return the global minimum energy configuration if they converge, and (2) those that are not guaranteed to return the global minimum energy configuration, but which will always return a solution. Examples of the first class of algorithms include but are not limited to Dead-End Elimination (DEE) and Branch & Bound (B&B) (including Branch and Terminate) (Gordon & Mayo, 1999, Structure Fold Des 7:1089-98). Examples of the second class of algorithms include, but are not limited to, Monte Carlo (MC), self-consistent mean field (SCMF), Boltzmann sampling (Metropolis et al., 1953, J Chem Phys 21:1087), simulated annealing (Kirkpatrick et al., 1983, Science, 220:671-680), genetic algorithm (GA), and Fast and Accurate Side-Chain Topology and Energy Refinement (FASTER) (Desmet, et al., 2002, Proteins, 48:31-43). A combinatorial optimization algorithm may be used alone or in conjunction with another combinatorial optimization algorithm.

In one embodiment of the present invention, the strategy for applying a combinatorial optimization algorithm is to find the global minimum energy configuration. In an alternate embodiment, the strategy is to find one or more low energy or favorable sequences. In an alternate embodiment, the strategy is to find the global minimum energy configuration and then find one or more low energy or favorable sequences. For example, as outlined in U.S. Ser. No. 6,269,312, preferred embodiments utilize a Dead End Elimination (DEE) step and a Monte Carlo step. In other embodiments, tabu search algorithms are used or combined with DEE and/or Monte Carlo, among other search methods (see Modern Heuristic Search Methods, edited by V. J. Rayward-Smith et al., 1996, John Wiley & Sons Ltd.; U.S. Ser. No. 10/218,102; and PCT WO 02/25588). In another preferred embodiment, a genetic algorithm may be used; see for example U.S. Ser. Nos. 09/877,695 and 10/071,859. As another example, as is more fully described in U.S. Pat. Nos. 6,188,965; 6,269,312; 6,403,312; 6,807,120; U.S. Ser. Nos. 09/782,004; 09/927,790; 10/218,102; PCT WO 98/07254; PCT WO 01/40091; and PCT WO 02/25588, the global optimum may be reached, and then further computational processing may occur, which generates additional optimized sequences. In the simplest embodiment, design calculations are not combinatorial. That is, energy calculations are used to evaluate amino acid substitutions individually at single variable positions. For other calculations it is preferred to evaluate amino acid substitutions at more than one variable position. In a preferred embodiment, all possible interaction energies are calculated prior to combinatorial optimization. In an alternatively preferred embodiment, energies may be calculated as needed during combinatorial optimization.

The present invention provides methods for generating libraries that may subsequently be screened experimentally to single out optimized polymerated (e.g. PEGylated) proteins. Again, in this context, "optimization" can refer to a optimal polymer attached to a specific polymer attachment site, as well as a protein that has been optimized for other properties, or both. For example, proteins that have an optimal biochemical property (altered binding to a receptor, for example) can also have optimized polymeric attachment sites and polymers. By "library" as used herein is meant a set of one or more sequences. Library may refer to the set of variants in any form. In one embodiment, the library is a list of nucleic acid or amino acid sequences, or a list of nucleic acid or amino acid substitutions at variable positions. For example, the examples used to illustrate the present invention below provide libraries as amino acid substitutions at variable positions. In one embodiment, a library is a list of at least one sequence that are variants optimized for a desired property. For example see, Filikov et al., 2002, Protein Sci 11:1452-1461 and Luo et al., 2002, Protein Sci 11:1218-1226. In an alternate embodiment, a library may be defined as a combinatorial list, meaning that a list of amino acid substitutions is generated for each variable position, with the implication that each substitution is to be combined with all other designed substitutions at all other variable positions. In this case, expansion of the combination of all possibilities at all variable positions results in a large explicitly defined library. A library may refer to a physical composition of polypeptides, a domain or fragment thereof. Thus a library may refer to a physical composition of proteins, antibodies or Fc fusions, either in purified or unpurified form. A library may refer to a physical composition of nucleic acids that encode the library sequences. Said nucleic acids may be the genes encoding the library members, the genes encoding the library members with any operably linked nucleic acids, or expression vectors encoding the library members together with any other operably linked regulatory sequences, selectable markers, fusion constructs, and/or other elements. For example, the library may be a set of mammalian expression vectors that encode library members, the protein products of which may be subsequently expressed, purified, and screened experimentally. As another example, the library may be a display library. Such a library could, for example, comprise a set of expression vectors that encode library members operably linked to some fusion partner that enables phage display, ribosome display, yeast display, bacterial surface display, and the like.

The library may be generated using the output sequence or sequences from computational screening. As discussed above, computationally generated libraries are significantly enriched in stable, properly folded, and functional sequences relative to randomly generated libraries. As a result, computational screening increases the chances of identifying proteins that are optimized for the design goal. The set of sequences in a library is generally, but not always, significantly different from the parent sequence, although in some cases the library preferably contains the parent sequence. As is known in the art, there are a variety of ways that a library may be derived from the output of computational screening calculations. For example, methods of library generation described in U.S. Pat. No. 6,403,312; U.S. Ser. Nos. 09/782, 004; 09/927,790; 10/218,102; PCT WO 01/40091; and PCT WO 02/25588 find use in the present invention. In one embodiment, sequences scoring within a certain range of the global optimum sequence may be included in the library. For example, all sequences within 10 kcal/mol of the lowest energy sequence could be used as the library. In an alternate embodiment, sequences scoring within a certain range of one or more local minima sequences may be used. In a preferred embodiment, the library sequences are obtained from a filtered set. Such a list or set may be generated by a variety of methods, as is known in the art, for example using an algorithm such as Monte Carlo, B&B, or SCMF. For example, the top $10^3$ or the top $10^5$ sequences in the filtered set may comprise the library. Alternatively, the total number of sequences defined by the combination of all mutations may be used as a cutoff criterion for the library. Preferred values for the total number of recombined sequences range from 10 to $10^{20}$, particularly preferred values range from 10 to $10^9$. Alternatively, a cutoff may be enforced when a predetermined number of mutations per position is reached. In some embodiments, sequences that do not make the cutoff are included in the library. This may be desirable in some situations, for instance to evaluate the approach to library generation, to provide controls or comparisons, or to sample additional sequence space. For example, the parent sequence may be included in the library, even if it does not make the cutoff.

Another type of covalent modification of protein included within the scope of this invention comprises altering the native glycosylation pattern of the target protein. "Altering the native glycosylation pattern" is intended for purposes herein to mean deleting one or more carbohydrate moieties found in the target protein, and/or adding one or more glycosylation sites that are not present in the target protein. Addition of glycosylation sites may be accomplished by altering the amino acid sequence thereof. The alteration may be made, for example, by the addition of, or substitution by, one or more serine or threonine residues to the native sequence (for O-linked glycosylation sites). The target amino acid sequence may optionally be altered through changes at the DNA level, particularly by mutating the DNA encoding the target polypeptide at preselected bases such that codons are generated that will translate into the desired amino acids.

Addition of N-linked glycosylation sites to target proteins may be accomplished by altering the amino acid sequence thereof. The alteration may be made, for example, by the addition of, or substitution by, one or more asparagine residues to the native sequence or target sequence. The modification may be made for example by the incorporation of a canonical N-linked glycosylation site, including but not limited to, N—X—Y, where X is any amino acid except for proline and Y is preferably threonine, serine or cysteine. Another means of increasing the number of carbohydrate moieties on a target polypeptide is by chemical or enzymatic coupling of glycosides to the polypeptide. Such methods are described in the art, e.g., in WO 87/05330 published 11 Sep. 1987, and in Aplin and Wriston, CRC Crit. Rev. Biochem., pp. 259-306 (1981).

Removal of carbohydrate moieties present on a target polypeptide may be accomplished chemically or enzymatically or by mutational substitution of codons encoding for amino acid residues that serve as targets for glycosylation. Chemical deglycosylation techniques are known in the art and described, for instance, by Hakimuddin, et al., Arch. Biochem. Biophys., 259:52 (1987) and by Edge et al., Anal. Biochem., 118:131 (1981). Enzymatic cleavage of carbohydrate moieties on polypeptides can be achieved by the use of a variety of endo-and exo-glycosidases as described by Thotakura et al., Meth. Enzymol., 138:350 (1987).

Such derivatized moieties may improve the solubility, absorption, and permeability across the blood brain barrier biological half life, and the like. Such moieties or modifications of target polypeptides may alternatively eliminate or attenuate any possible undesirable side effect of the protein and the like. Moieties capable of mediating such effects are disclosed, for example, in Remington's Pharmaceutical Sciences, 16th ed., Mack Publishing Co., Easton, Pa. (1980).

EXAMPLES

Example 1

Optimized PEGylation of Erythropoietin

It is well known in the art that non-glycosylated erythropoietin (EPO) and EPO variants do not possess significant levels of in vivo biological activity. This is most likely a result of the rapid in vivo turnover of non-glycosylated EPO. Site-specific incorporation of glycosylation sites serves as a successful approach for improving PK. A notable example is Amgen's hyperglycosylated erythropoietin variant Aranesp® (darbepoetin alfa), engineered to contain two additional N-linked glycosylation sites. The additional glycosylation increases the serum half-life 3-fold. However, the same modifications reduce in vitro specific activity roughly 4-fold, indicating a need for EPO analogs that have both improved PK and high specific activity. There is a thus need for improvements in chemical or posttranslational modification of proteins to modification sites that maximally improve pharmacokinetic properties while minimizing the effect on the structural and functional properties of the protein.

Figure 2:
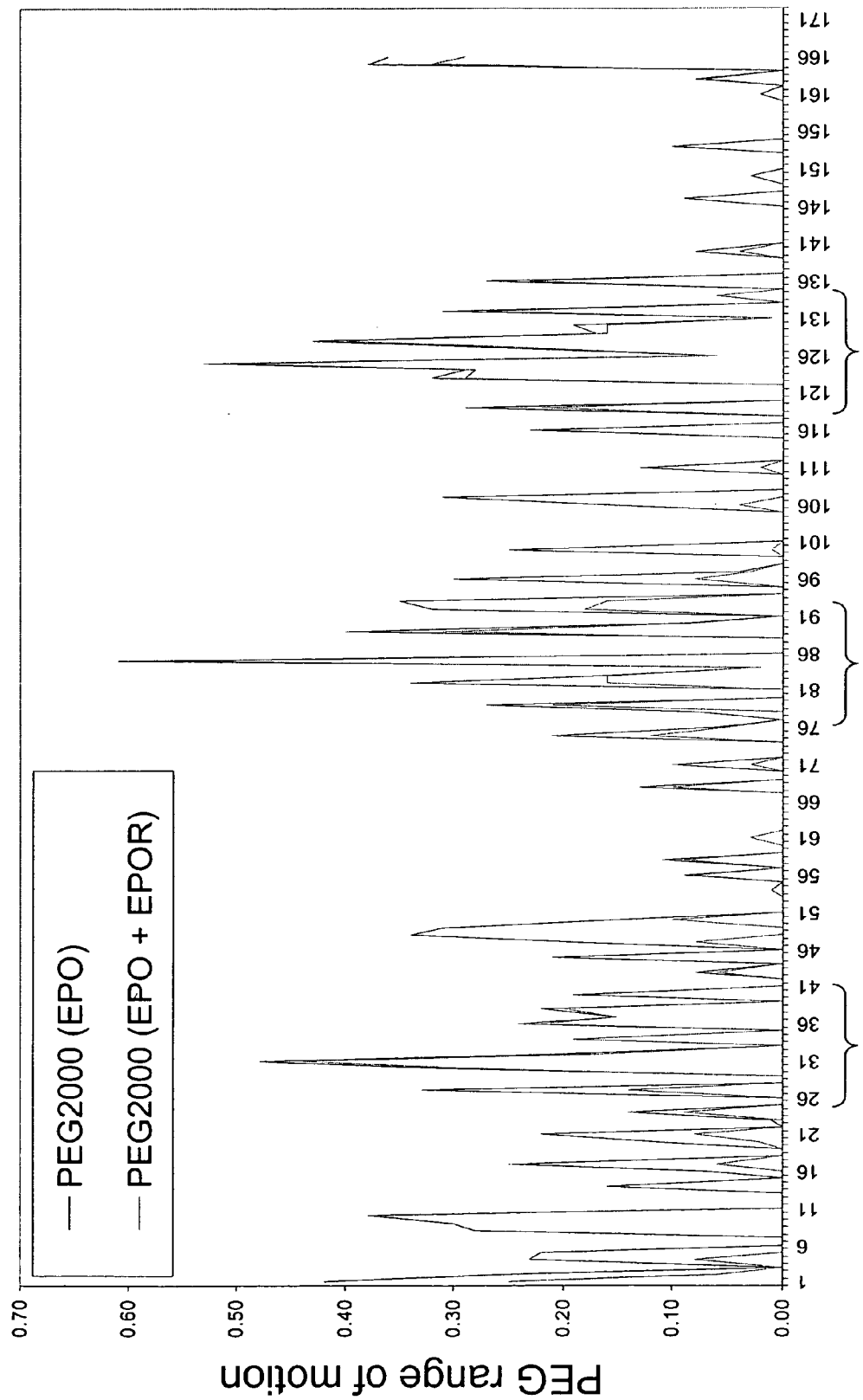
FIG. 2 shows simulation results for PEG2000 attached at all amino acid positions of EPO. The top line in the chart represents the fractional degrees of freedom for attached PEG in the context of EPO alone. The bottom line represents the fractional degrees of freedom for attached PEG in the context of the EPO/EPO receptor complex.
Figure 3:
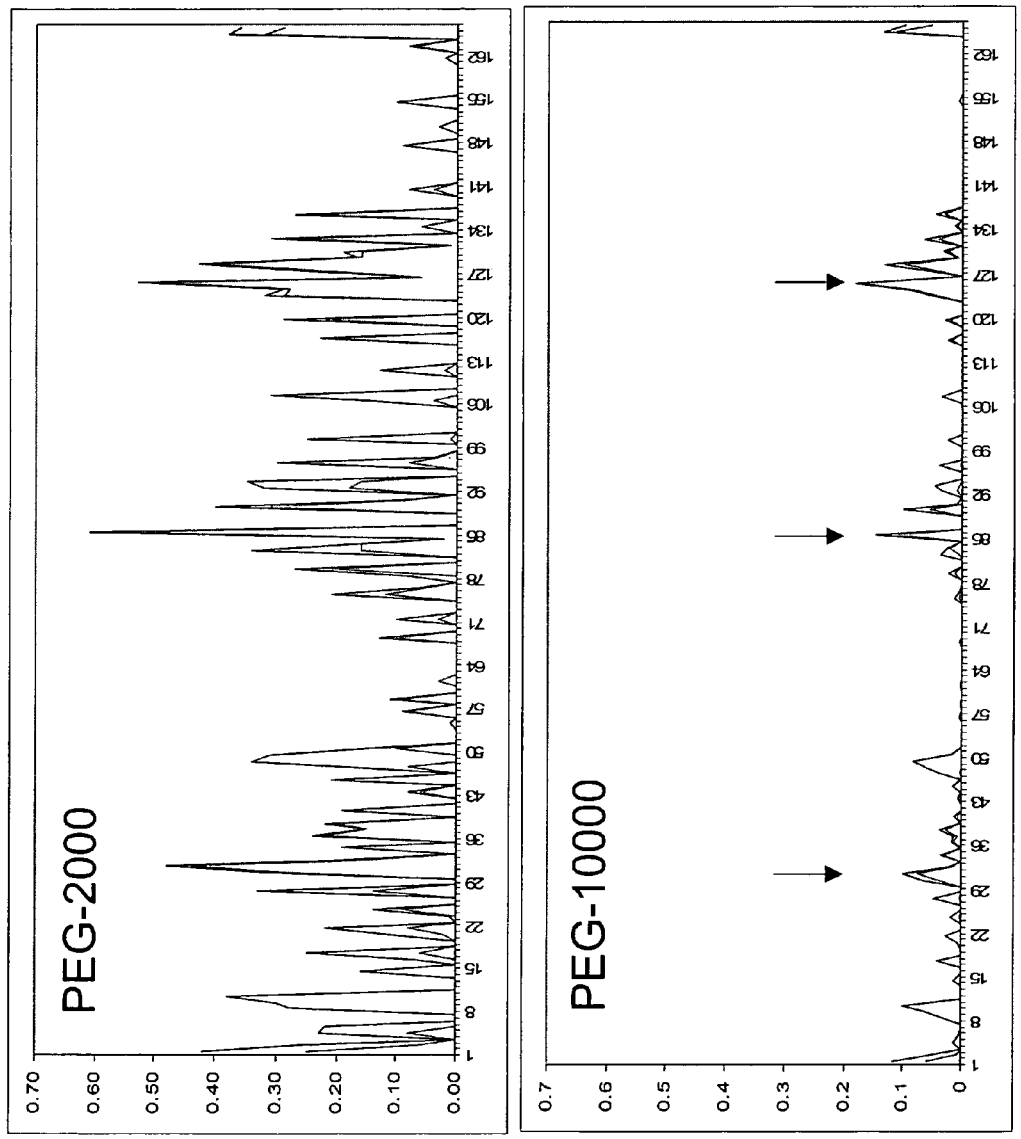
FIG. 3 is a comparison showing the dependence of PEG size.
Figure 4:
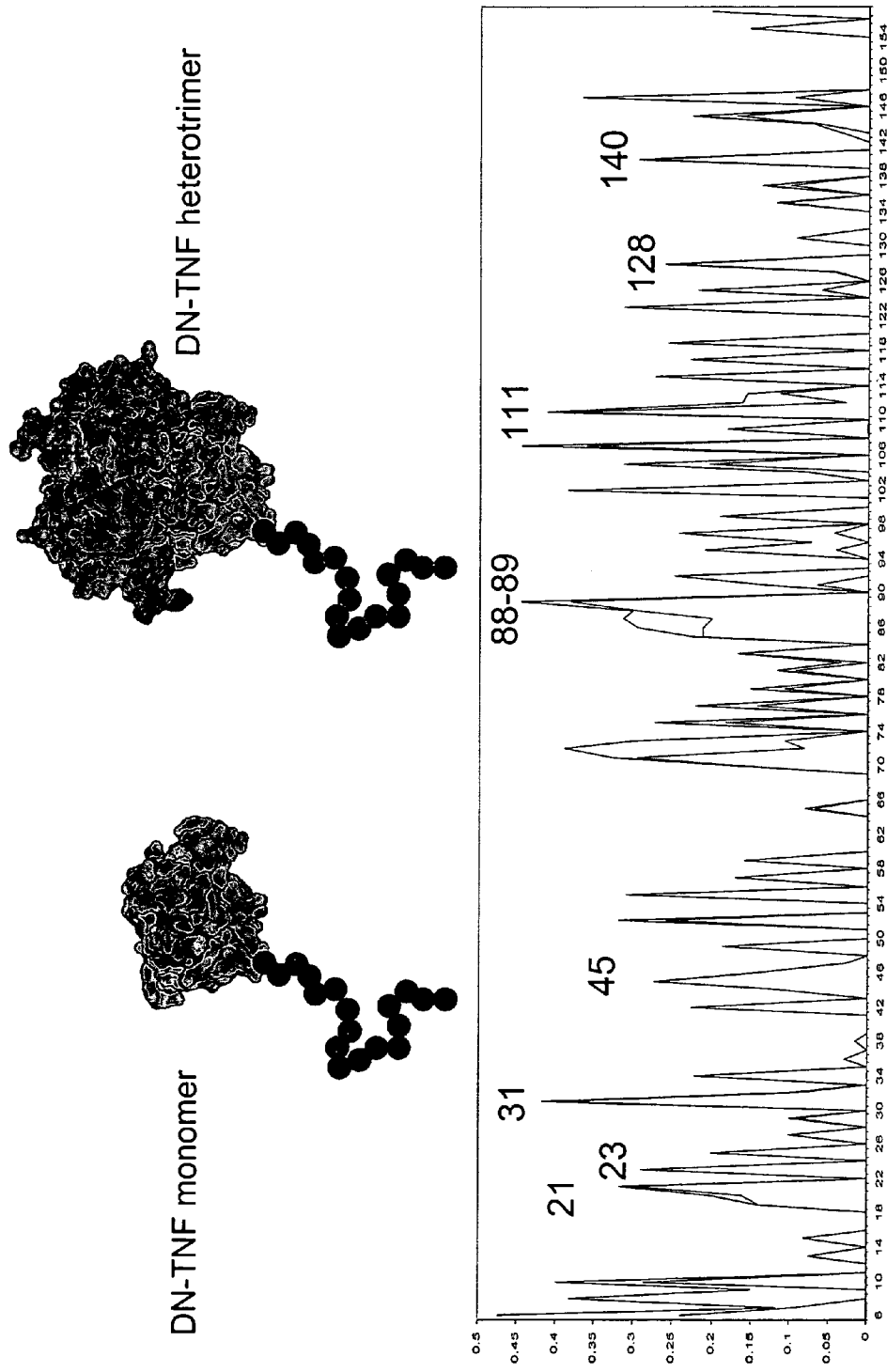
FIG. 4 shows a simulation of the optimization of PEGylation for Dominant Negative-Tumor Necrosis Factor (DN-TNF). Simulation of PEG degrees of freedom in the context of DN-TNF monomer versus trimer reveals optimal PEGylation sites for preserving the DN-TNF mechanism of action.
Figure 5:
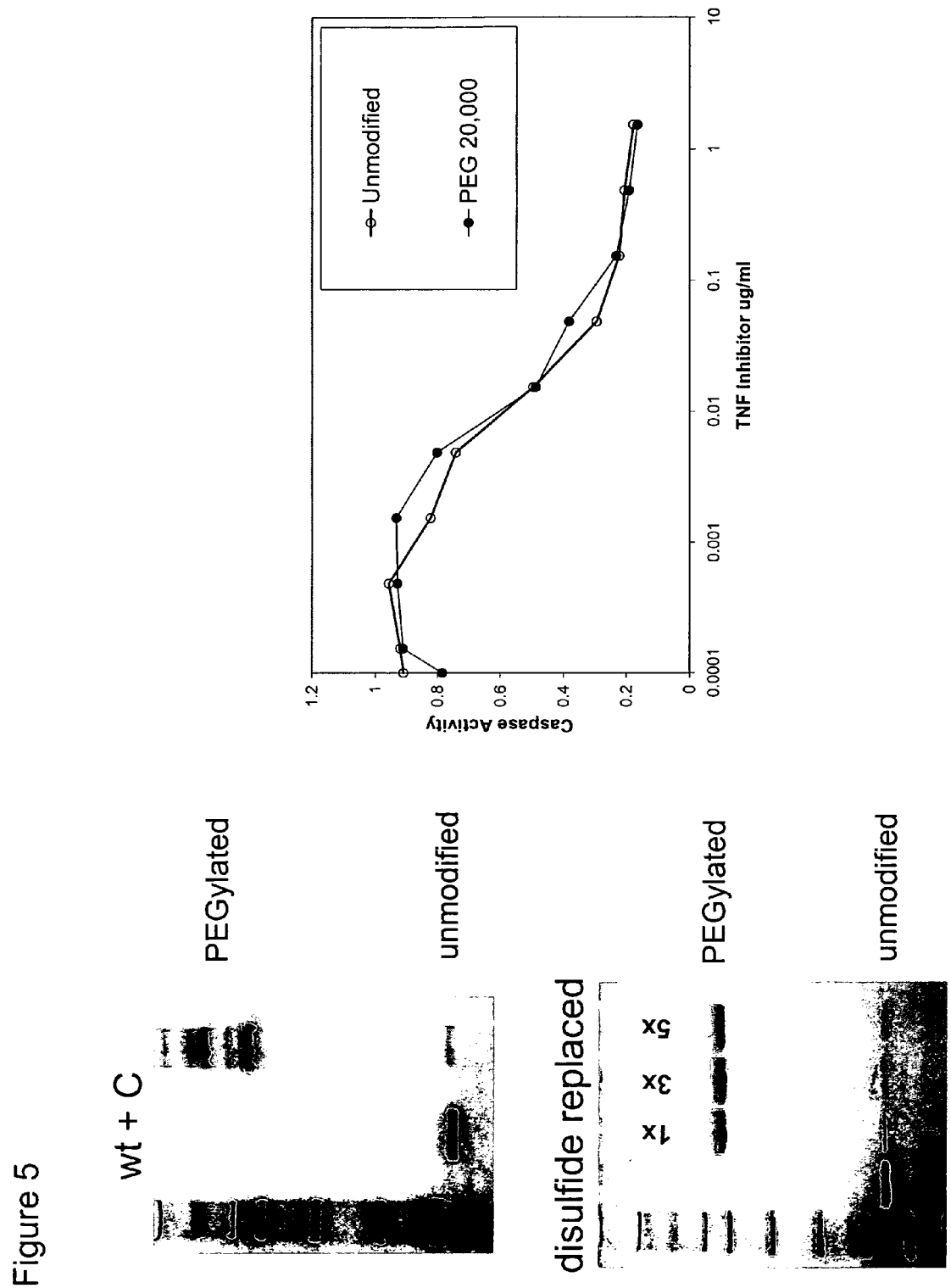
FIG. 5 show gels of the PEGylation of DN-TNF at position 31. Native gels reveal that PEGylation is extremely efficient for the R31C variant of a DN-TNF molecule. The lower gel shows that replacement of a labile disulfide naturally occurring in TNF leads to more homogeneously PEGylated material, where the sole PEGylation site is position 31. Activity assays show that the R31C PEGylation with PEG-20000 does not decrease activity relative to the unmodified material.
Figure 6:
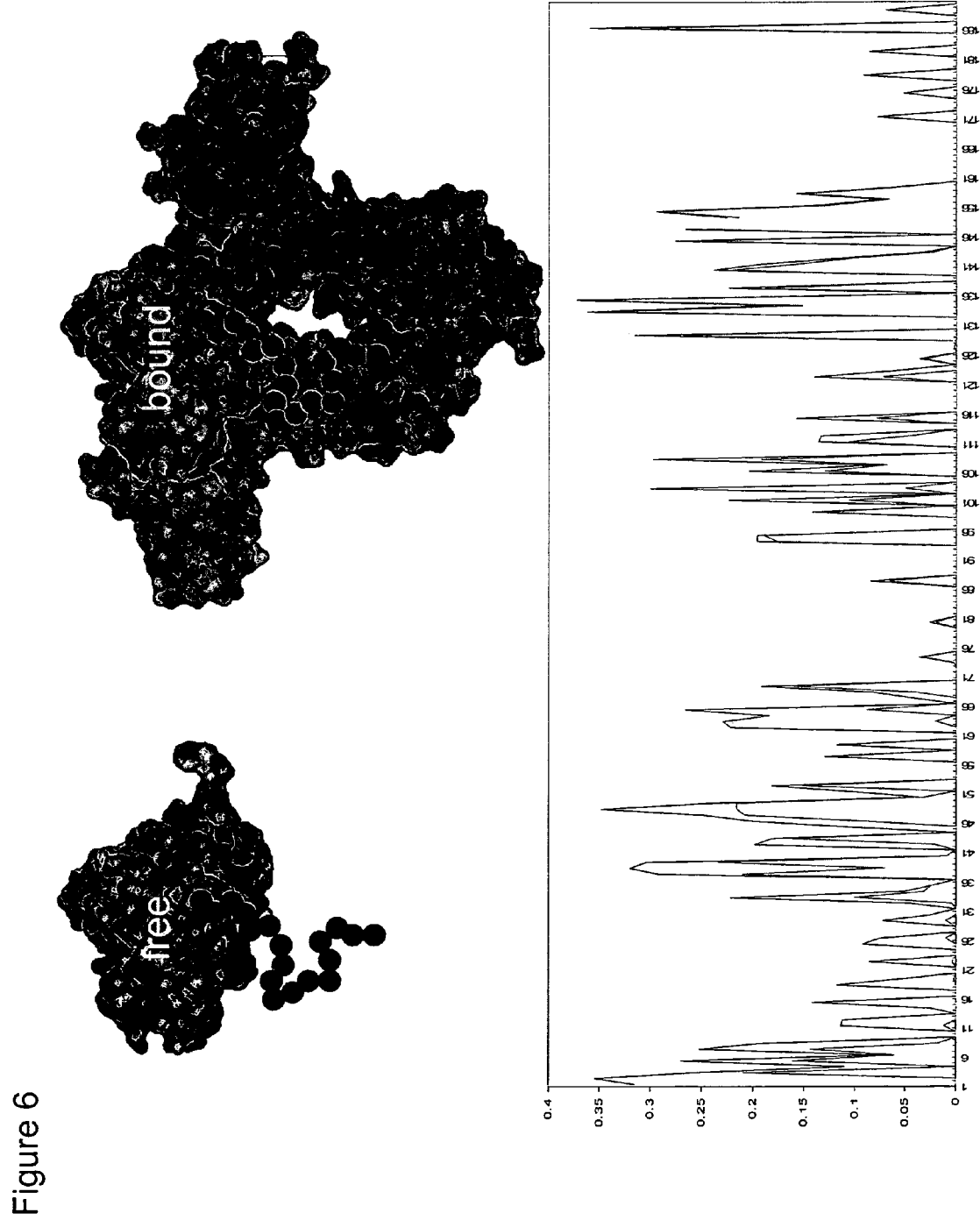
FIG. 6 shows the optimization of PEG sites for human growth hormone using a PEG size of 5000.
Figure 7:
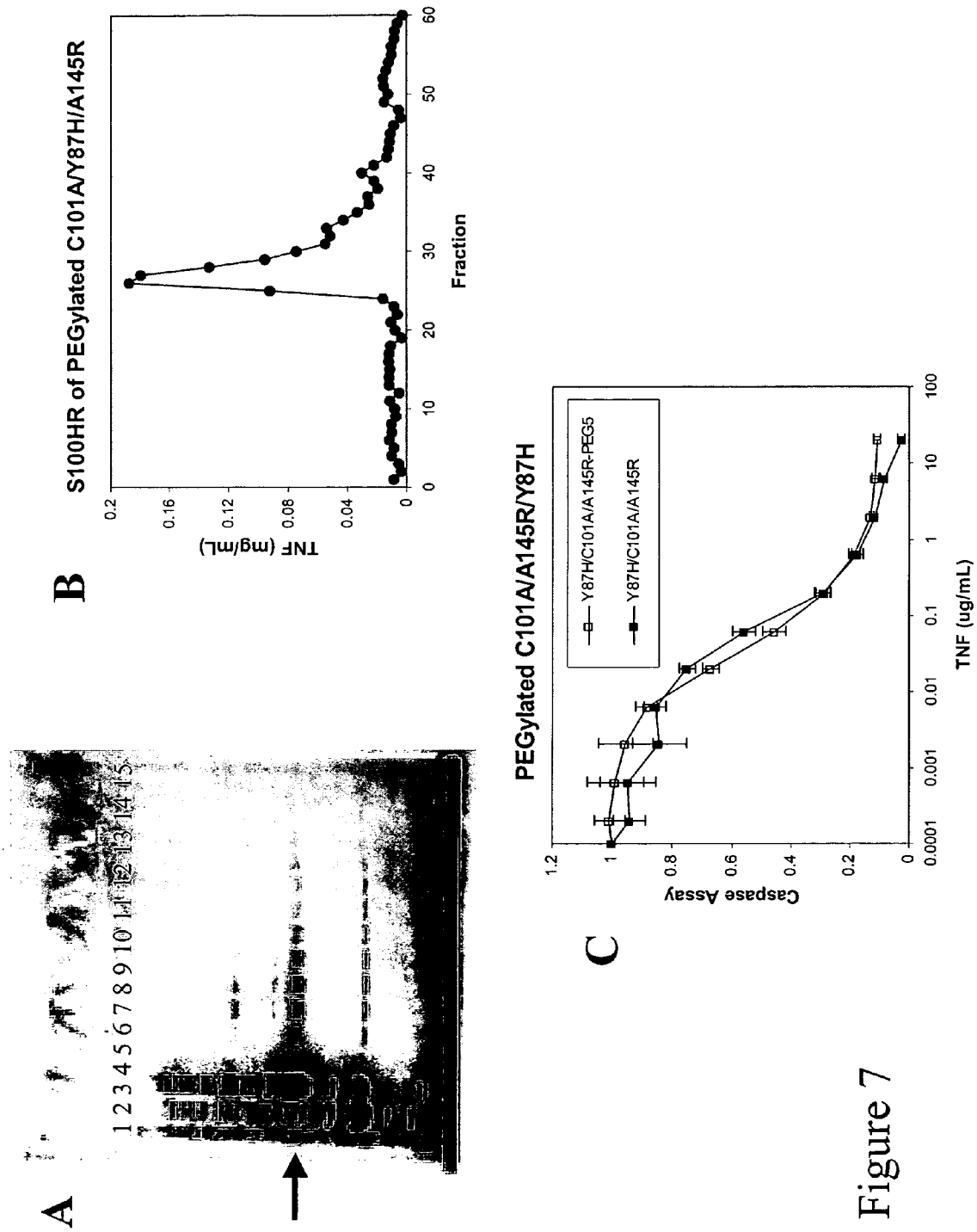
FIG. 7 shows the retention of bioactivity of TNF variant R31C/C69V/Y87H/C101A/A145R PEGylated with different sized PEG moieties. The bioactivity of these conjugated proteins was determined via caspase assay (as in FIG. 7C) and compared to etanercept.
Figure 8:
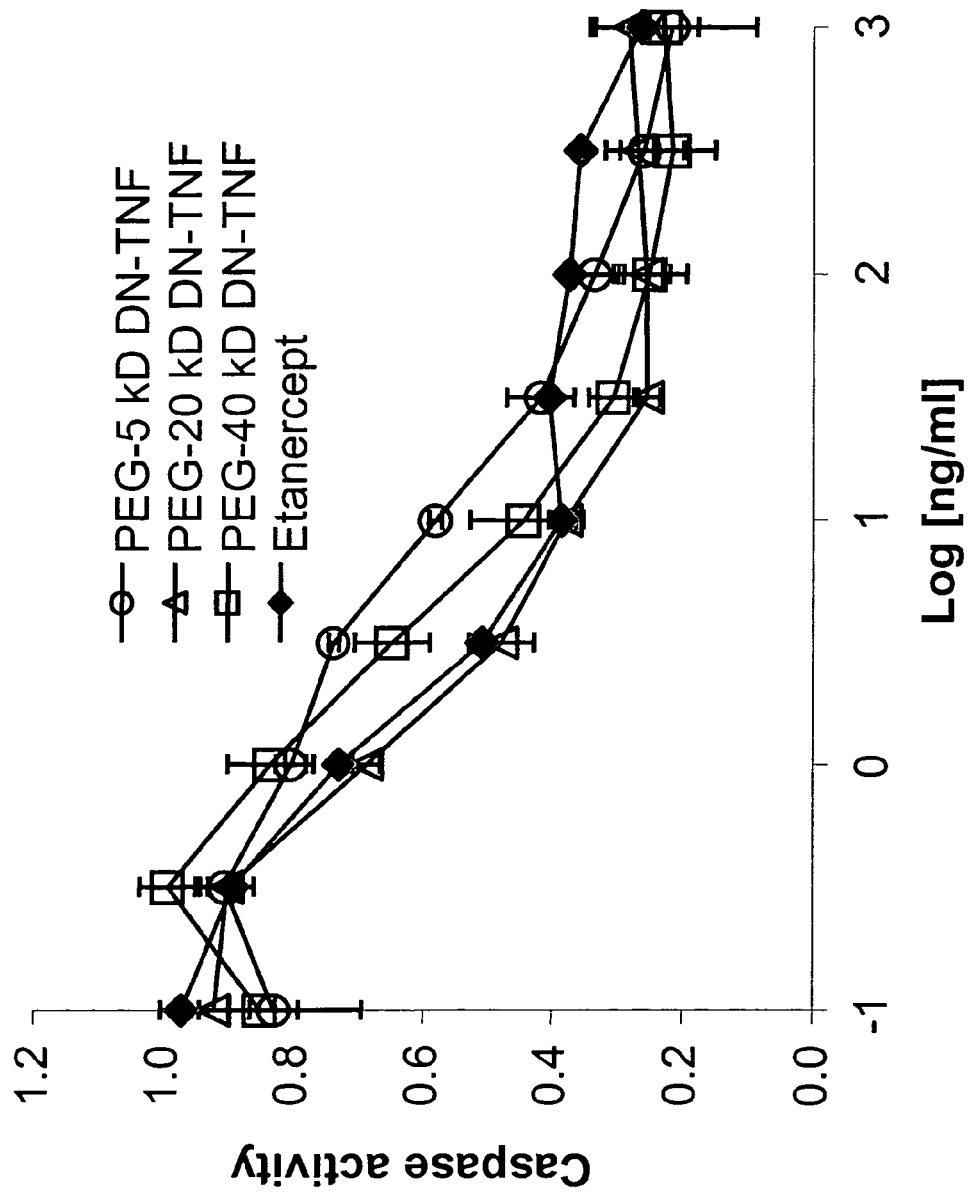
FIG. 8 shows PEGylated TNF variant R31C/C69V/Y87H/C101A/A145R has improved pharmacokinetics.

The range of motion for PEG moieties attached to the isolated EPO protein (derived from PDB file 1EER by deleting the receptor coordinates) depends dramatically on the site of attachment (FIG. 2) and the size of the attached PEG (FIG. 3). As seen in Table 1 (free column), and FIG. 2, the simulation results indicate that the highest efficiency coupling sites are positions Glu31, Ser85, and Ala125. In a preferred embodiment, one or more of these residues will be substituted with cysteine residues to enable the site-specific attachment of a PEG using chemistries and methods known in the art.

The ratio of the ranges of motion of the PEG for EPO alone versus EPO complexed with its receptor relates to the loss of activity that ensues when PEG is coupled at a specific site in the protein. Simulations using the crystal structure of EPO alone and the structure of the EPO/EPOR complex (using PDB file 1 EER) predict that the effect of PEGylation on EPO activity also depends dramatically on the site of attachment (FIG. 2) and the size of the attached PEG (FIG. 3). A list of ratios is shown in Table 1, in rank order of highest ratio to lowest ratio for simulation of a PEG moiety with molecular weight 2000 daltons. Table 1 shows that positions in the vicinity of Ser34, Asn84, and Ala124 are optimal PEG attachment sites. In other words, attachment of a PEG moiety to any of these sites should have minimal effect on the activity of the EPO analog. The three sites with optimal predicted coupling efficiencies (Glu31, Ser85, and Ala125) have high ratios as well, suggesting that these sites are the best compromise between coupling efficiency, stability, and functional activity. The three sites are similarly identified for PEG10000 (see FIG. 3). Independence from PEG size indicates that preferred sites will also be ideal for attachment of any polymer moiety with a high degree of flexibility.

TABLE 1

| | | SASA | FASA | free receptor ratio | | |
|---|---|---|---|---|---|---|
| SER | 34 | 56.3 | 0.40 | 0.19 | 0.190 | 1.000 |
| GLU | 37 | 54.8 | 0.30 | 0.15 | 0.150 | 1.000 |
| ALA | 124 | 75 | 0.60 | 0.29 | 0.280 | 0.966 |
| THR | 40 | 58.1 | 0.40 | 0.19 | 0.180 | 0.947 |
| ALA | 125 | 113.4 | 1.00 | 0.53 | 0.500 | 0.943 |
| ASN | 83 | 135.7 | 0.60 | 0.17 | 0.160 | 0.941 |
| PRO | 129 | 125.1 | 0.90 | 0.17 | 0.160 | 0.941 |
| ALA | 128 | 59.3 | 0.50 | 0.43 | 0.400 | 0.930 |
| ASN | 36 | 106.5 | 0.60 | 0.24 | 0.220 | 0.917 |
| GLU | 31 | 169.2 | 0.90 | 0.48 | 0.440 | 0.917 |
| LYS | 116 | 147.4 | 0.70 | 0.23 | 0.210 | 0.913 |
| ASN | 38 | 137.3 | 0.60 | 0.22 | 0.200 | 0.909 |
| ASP | 123 | 117.1 | 0.70 | 0.32 | 0.290 | 0.906 |
| ALA | 30 | 63.2 | 0.50 | 0.32 | 0.290 | 0.906 |
| SER | 85 | 118.3 | 0.90 | 0.61 | 0.550 | 0.902 |
| ALA | 127 | 77.5 | 0.70 | 0.26 | 0.230 | 0.885 |
| THR | 132 | 98.6 | 0.60 | 0.31 | 0.270 | 0.871 |
| ASP | 136 | 80.1 | 0.50 | 0.27 | 0.230 | 0.852 |
| ASP | 165 | 157.8 | 1.00 | 0.38 | 0.320 | 0.842 |
| LEU | 130 | 135.7 | 0.70 | 0.19 | 0.160 | 0.842 |
| GLN | 58 | 58.4 | 0.30 | 0.11 | 0.090 | 0.818 |
| HIS | 32 | 81.3 | 0.40 | 0.21 | 0.170 | 0.810 |
| ARG | 166 | 173 | 0.70 | 0.36 | 0.290 | 0.806 |
| ALA | 79 | 40.5 | 0.30 | 0.27 | 0.210 | 0.778 |
| GLU | 89 | 161.3 | 0.90 | 0.40 | 0.310 | 0.775 |

TABLE 1-continued

|     | SASA | FASA |      |       | free receptor ratio |
|-----|------|------|------|-------|-------|
| ALA | 68   | 42.8 | 0.40 | 0.13  | 0.100 | 0.769 |
| ILE | 119  | 112.8| 0.60 | 0.29  | 0.220 | 0.759 |
| ALA | 50   | 43.6 | 0.40 | 0.15  | 0.100 | 0.667 |
| ASN | 24   | 105  | 0.50 | 0.14  | 0.090 | 0.643 |
| ALA | 1    | 92.6 | 0.80 | 0.42  | 0.250 | 0.595 |

A high ratio shows little or no difference at a specific site between free protein and reception bound protein. A position with low ratio is indicative of a position where chemical modification likely inhibits receptor binding.

Example 2

Optimized PEGylation of a Dominant-Negative TNF

Figure 9:
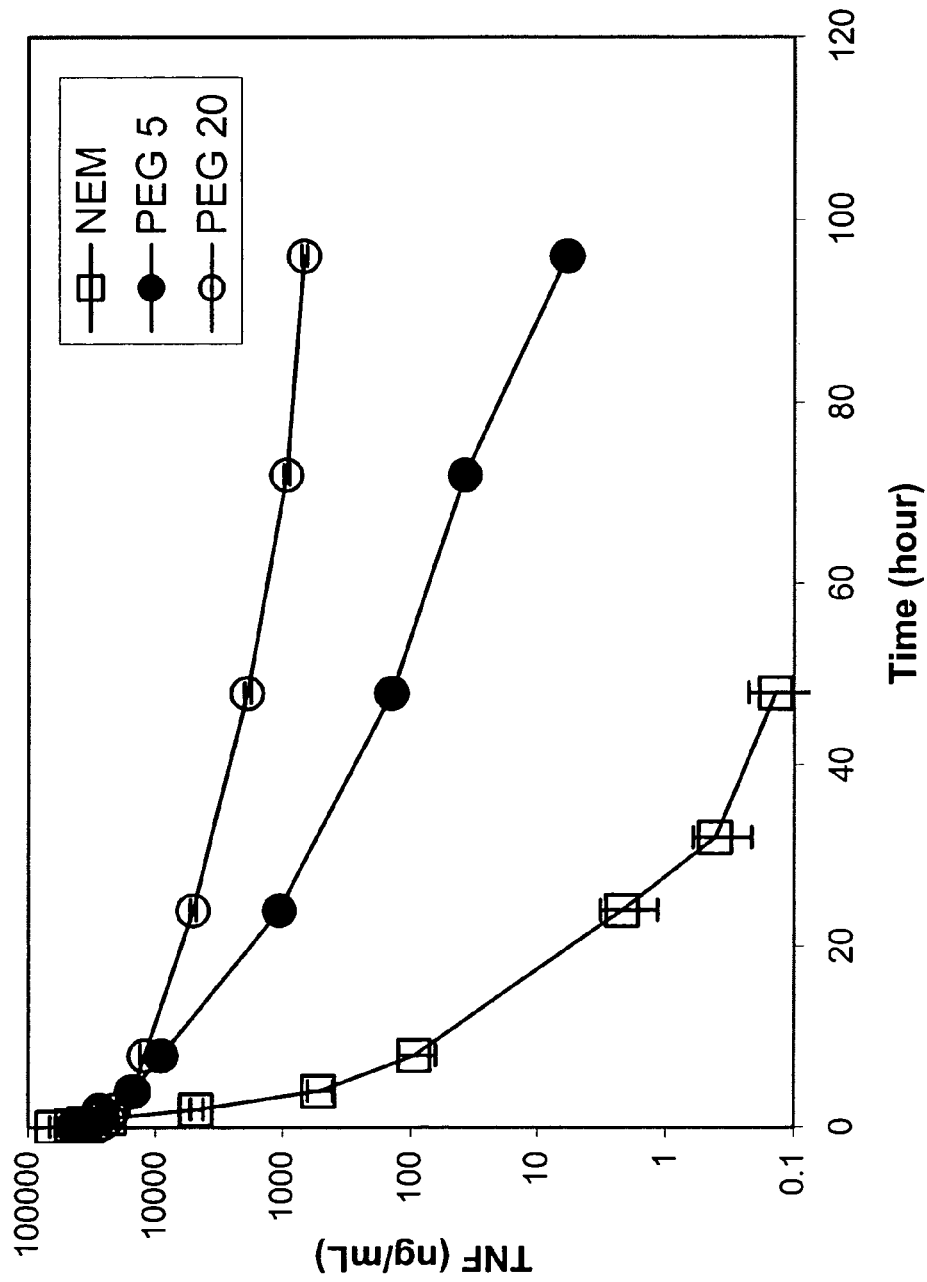
FIG. 9 shows pharmacokinetics (pK) data of PEGylated TNF variant R31C/C69V/Y87H/C101A/A145R.

Although cytokine-receptor binding is a common consideration for the design of optimal protein therapeutics, other mechanisms of action are possible. These mechanisms dictate that other considerations are necessary for optimization of PEG attachment sites. The development of dominant-negative variants of TNF for the inhibition of endogenous TNF serves as a useful example (see U.S. Ser. No 10/262,630, filed Sep. 30, 2002; U.S. Ser. No. 09/981,289, filed Oct. 15, 2001; U.S. Ser. No. 09/945,150, filed Aug. 31, 2001; U.S. Ser. No. 09/798,789, filed Mar. 2, 2001; U.S. Ser. No. 60/186,427, filed Mar. 2, 2000; U.S. Ser. No. 60/510,454, filed Oct. 10, 2003; U.S. Ser. No. 60/509,960, filed Oct. 9, 2003; and U.S. Ser. No. 60/528,276, filed Dec. 8, 2003, all of which are incorporated by reference in their entirety).

The active form of TNF is a noncovalent trimer. Dominant-negative variants of TNF (DN-TNF) have been created by removing their ability to bind or signal through TNF receptors (TNFR) while maintaining their ability to exchange and coassemble with endogenous wild-type TNF proteins to form inactive heterotrimers. These heterotrimers are composed of wild-type and variant subunits in 1:2 or 2:1 ratios. PEGylation of DN-TNF proteins is desirable to extend their in vivo half-life. However, optimal PEGylation sites are those that minimally perturb the ability of DN-TNF monomers to coassemble with wild-type monomers. The methods of the present invention have been used to select optimal cysteine PEGylation sites in the DN-TNF proteins. Optimal sites include, but are not limited to 21, 23, 31, 45, 88, 89, 111, 128, and 140 (see FIG. 4). A DN-TNF variant was modified with a R31C mutation to enable site specific PEGylation at position 31 using chemistries commercially available from Nektar Therapeutics. As shown in FIG. 5, PEGylation at this site was efficient and had no detectable effect on activity with a PEG moiety of molecular weight 20,000 Da. Additional experiments showed that PEGs of higher and lower molecular weight also had no detectable effect on activity.

Example 3

Optimized PEGylation of Human Growth Hormone (HGH)

HGH is used to treat growth-related disorders. As with most therapeutic proteins, its PEGylation is expected to improve its pharmacokinetic properties in a patient. The methods of the present invention have been used to select optimal PEGylation sites in HGH (see FIG. 6). Further analysis of the simulation data indicate that optimal PEGylation sites on HGH include, but are not limited to Ala155, Ser95, Thr135, Pro133, Ser57, Lys158, Asp154, Asn99, Lys140, Lys145, and Asp147, or equivalent positions in variants. As discussed above, site specific PEGylation at any of these or other positions would require replacement of the native amino acid with a suitable amino acid such as cysteine. Alternatively, because Lys158 and Lys145 are good PEGylation sites, all other lysines in HGH can be replaced so that specific PEGylation at positions 145 and 158 is enabled.

Example 4

Optimized PEGylation of Interferon-b.

Interferon-b (IFN-b) is used to treat multiple sclerosis. As with most therapeutic proteins, its PEGylation is expected to improve its pharmacokinetic properties in a patient. Furthermore, since IFN-b is known to aggregate, PEGylation may also improve its solution properties. The structure of IFN-b with its receptor has not yet been determined, although mutagenesis studies have been performed to determine sites in the protein that interact with receptor. In this case, the methods of the present invention are used to locate PEGylation sites that have efficient coupling and will not destabilize the protein. Comparison of these sites with those determined by mutagenesis studies to interact with receptor indicates that optimal PEGylation sites are Lees 108, Asp110, and Asn166, or equivalent positions in variants. As discussed above, site specific PEGylation at any of these or other positions would require substitution with a suitable amino acid such as cysteine.

Example 5

Rational PEGylation of DN-TNF Produces Bioactive Protein

The technology described in this invention was used to determine that amino acid position 31 would be an ideal candidate for site-specific modification and it was particularly well exposed to solution. To avoid a non-specific chemical reaction, a DN-TNF variant was generated that lacked endogenous cysteines and contained an engineered cysteine only at position 31 (R31C/C69V/Y87H/C101A/A145R TNF-a). This protein was expressed, purified, and labeled with a 10-fold excess of maleimide-conjugated PEG-5000, PEG-20000, and PEG40000 in PBS. The protein was processed and prepared as described above except that purification away from free-PEG was accomplished via cation exchange. The bioactivity of these conjugated proteins was determined via caspase assay and compared to etanercept in FIG. 8. The molecules tested all retained the desired ability to inactivate TNF-induced cell signaling.

Example 6

Rationally PEGylated TNF-a has Improved Pharmacokinetics

Native TNF-a has a relatively poor pK profile in either rat or mouse. It was demonstrated that rational PEGylation of R31C/C69V/Y87H/C101A/A145R TNF-a could vastly improve this protein's pK properties. Three normal rats were injected with a 1 mg/kg intravenous dose of either PEGylated or unPEGylated unconjugated R31C/C69V/Y87H/C101A/A145R DN-TNF variant, namely, (NEM), PEG-5000, or PEG-20000. Plasma samples from these animals were continually recovered over a 100 hour time-course and concentration of the molecules was determined via a standard ELISA directed against human TNF. FIG. 9 shows that PEGylated TNF variant R31C/C69V/Y87H/C101A/A145R showed improved pharmacokinetics. In addition, it was observed that it was consistent in that larger PEG sizes result in longer circulation times.

Example 7

Optimized PEGylation of Granulocyte Colony Stimulating Factor (G-CSF)

Figure 10:
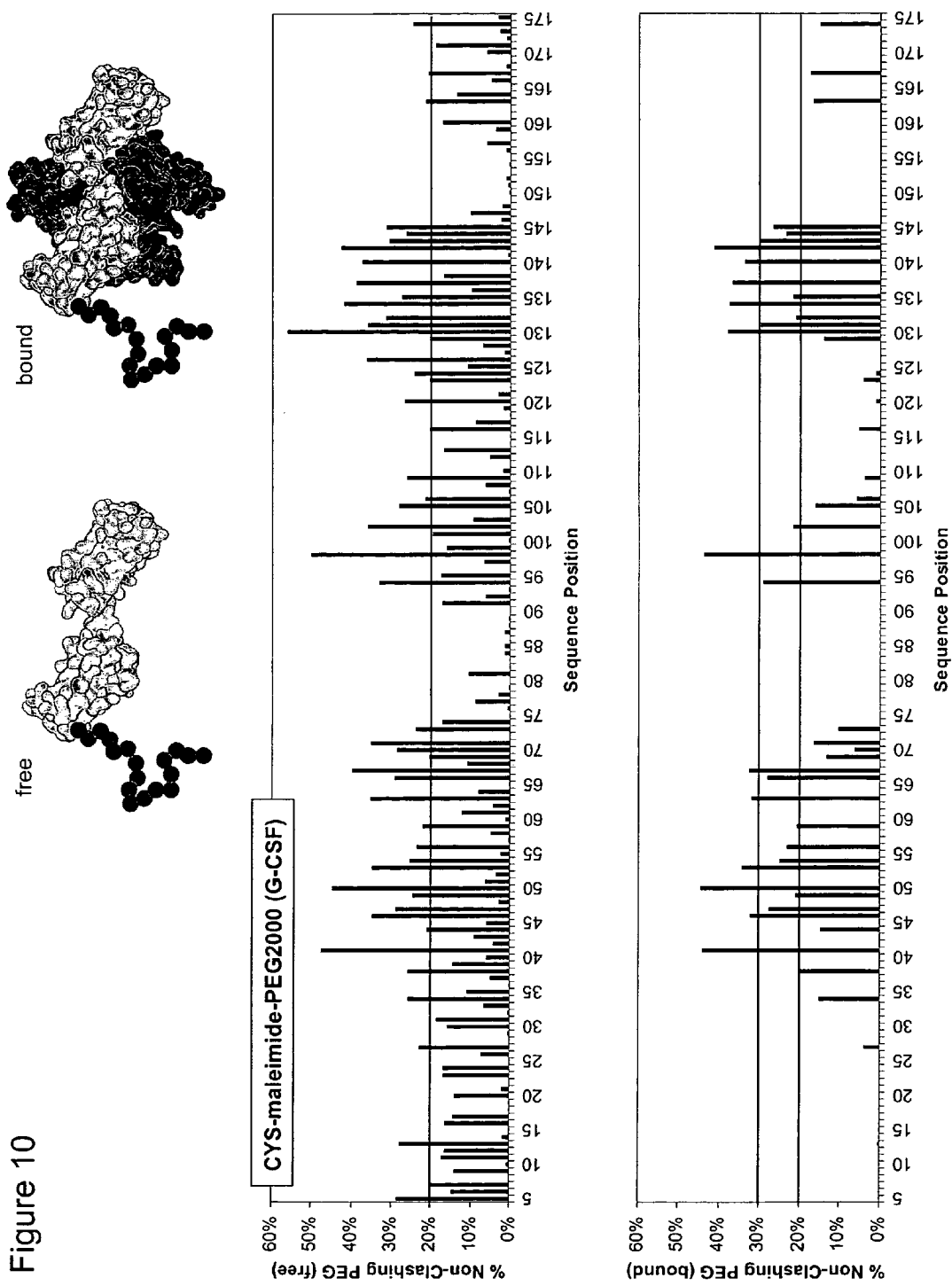
FIG. 10 shows the optimization of PEG sites for granulocyte colony stimulating factor (G-CSF) using a PEG size of 2000 and using a cysteine-maleimide attachment moiety.
Figure 11:
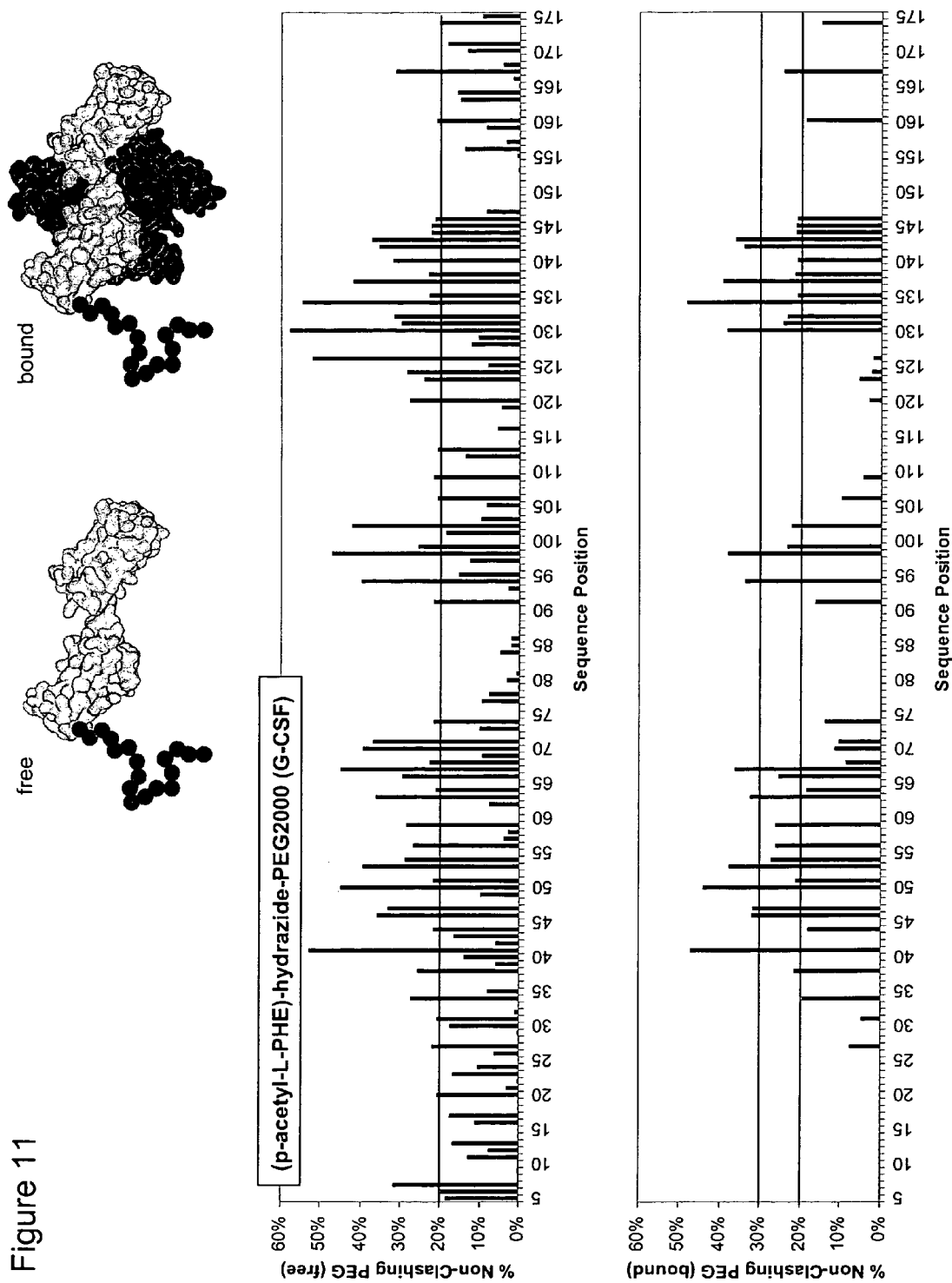
FIG. 11 shows the optimization of PEG sites for granulocyte colony stimulating factor (G-CSF) using a PEG size of 2000 and using a (p-acetyl-L-phenylalanine)-hydrazide attachment moiety.

G-CSF is used to treat leukemia and other cancers as well as other conditions such as pneumonia and leukopenia. As with most therapeutic proteins, its PEGylation is expected to improve its pharmacokinetic properties in a patient. The methods of the present invention have been used to select optimal PEGylation sites in G-CSF using both cysteine-maleimide attachment moiety (see FIG. 10) and p-acetyl-L-phenylalanine attachment moiety (see FIG. 11) based on Protein Data Bank structure 1CD9, chain A (G-SCF) and chains B and D (G-SCF receptor). The simulation data was first analyzed to identify sites with high coupling efficiency. For PEG2000, sites for which greater than 20% of the simulated PEG chains are non-clashing in the free state are considered optimal sites for attachment (see FIGS. 10 and 11, top chart). These sites include Gly5, Ala7, Ser3, Gly27, Glu34, Ala38, Lys41, His44, Glu46, Glu47, Val49, Leu50, His53, Ser54, Gly56, Trp59, Ser63, Pro66, Ser67, Ala69, Leu70, Gln71, Ala73, Glu94, Pro98, Pro102, Asp105, Thr106, Leu109, Thr116, Gln120, Glu123, Glu124, Gly126, Pro129, Ala130, Leu131, Gln132, Thr134, Gln135, Ala137, Ala140, Ala142, Ser143, Ala144, Phe145, Glu163, Arg167, and Gln174, or equivalent positions in variants.

The predicted high coupling efficiency sites were further screened to identify which of these sites retain PEG range of motion upon receptor binding. For PEG2000, sites for which greater than 20% of the simulated PEG chains are non-clashing in the bound state are preferred (see FIGS. 10 and 11, bottom chart). These sites include Ala38, Lys41, Glu46, Glu47, Val49, Leu50, His53, Ser54, Gly56, Trp59, Ser63, Pro66, Ser67, Glu94, Pro98, Pro102, Ala130, Leu131, Gln132, Thr134, Gln135, Ala137, Ala140, Ala142, Ser143, Ala144, and Phe145. For PEG2000, sites for which greater than 30% of the simulated PEG are not clashing in the bound state are especially preferred. These sites include Ala38, Glu47, Val49, Ser54, Gly56, Trp59, Pro66, Glu94, Pro102, Gln132, Gln135, Ala144, and Phe145, or equivalent positions in variants.

As discussed above, site specific PEGylation at any of these or other positions would either require replacement of the native amino acid with a suitable amino acid such as cysteine or the introduction of an unnatural amino acid such as p-acetyl-L-phenylalanine. The set of optimal incorporation sites identified from simulation is not strongly dependent on attachment chemistry (see FIGS. 10 and 11). Independence from attachment chemistry indicates that preferred sites will be ideal for attachment of any polymer moiety with a high degree of flexibility (e.g., carbohydrate).

Example 8

Optimized PEGylation of Bone Morphogenetic Protein 7 (BMP7)

Figure 12:
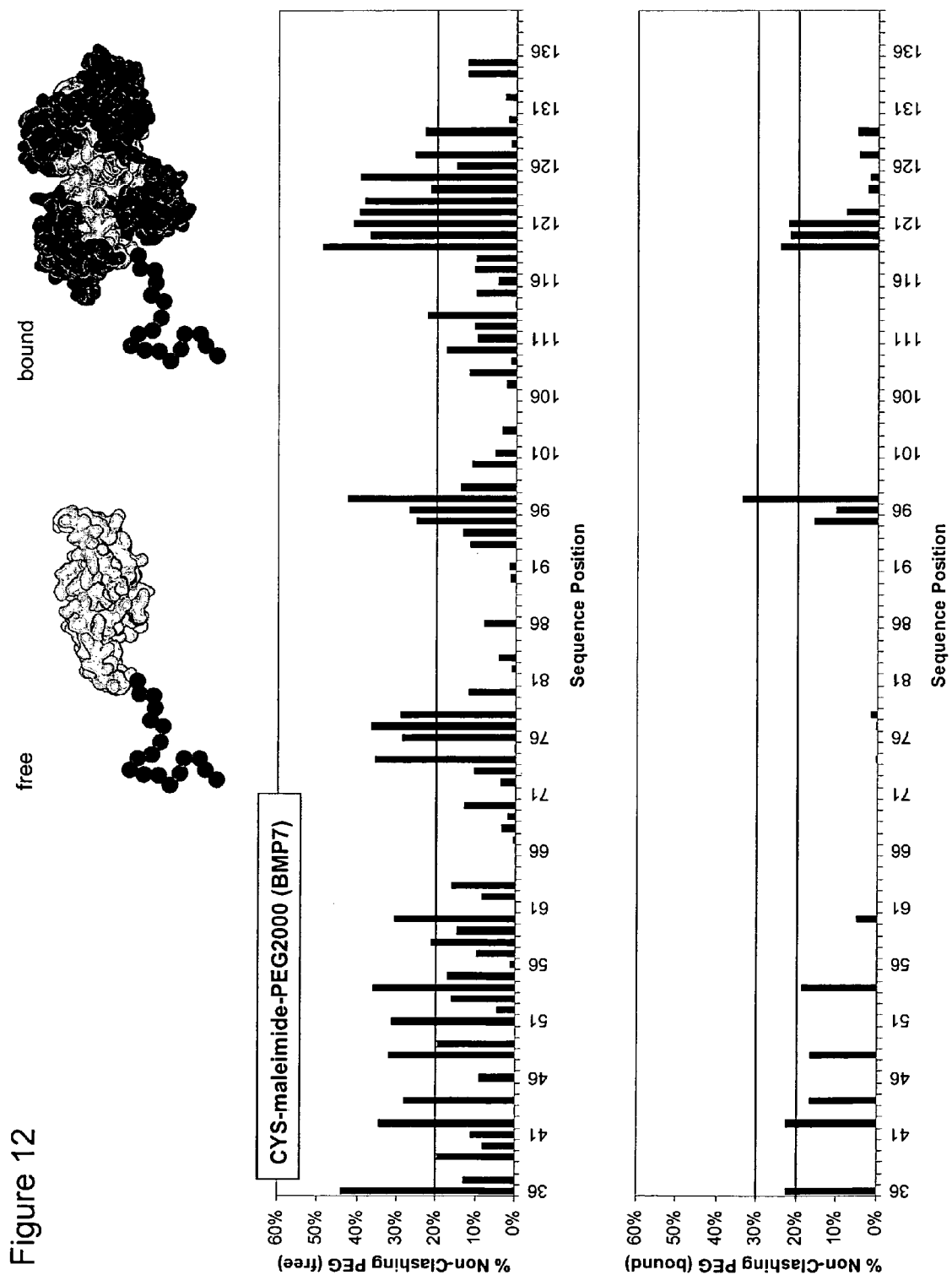
FIG. 12 shows the optimization of PEG sites for bone morphogenetic protein 7 (BMP7) using a PEG size of 2000.

As with most therapeutic proteins, the PEGylation of BMP7 is expected to improve its pharmacokinetic properties in a patient. The methods of the present invention have been used to select optimal PEGylation sites in BMP7 (see FIG. 12) based on a hexameric model of dimeric BMP7 (light and dark blue) complexed to pairs of type I (green) and type II receptors (red). The model was created using the structures of BMP7 complexed to ActRII and BMP-2 complexed to receptor Ia. The simulation data was first analyzed to identify sites with high coupling efficiency. For PEG2000, sites for which greater than 20% of the simulated PEG chains are non-clashing in the free state are considered optimal sites for attachment (see FIG. 12, top chart). These sites include Gln36, Glu42, Tyr44, Arg48, Gly51, Asp54, Ala58, Glu60, Pro74, Asn76, Ser77, Tyr78, Asn95, Pro96, Glu97, Ser113, Asp119, Ser120, Ser121, Asn122, Val123, Ile124, Leu125, Lys127, and Arg129.

The predicted high coupling efficiency sites were further screened to identify which of these sites retain PEG range of motion upon receptor binding. For PEG2000, sites for which greater than 20% of the simulated PEG chains are non-clashing in the bound state are preferred (see FIG. 12). These sites include Gln36, Glu42, Glu97, Asp119, Ser120, and Ser121. For PEG2000, sites for which greater than 30% of the simulated PEG are not clashing in the bound state are especially preferred. These sites include Glu97. As discussed above, site specific PEGylation at any of these or other positions would either require replacement of the native amino acid with a suitable amino acid such as cysteine or the introduction of an unnatural amino acid such as p-acetyl-L-phenylalanine.

All cited references are hereby incorporated by reference in their entirety.

Whereas particular embodiments of the invention have been described above for purposes of illustration, it will be appreciated by those skilled in the art that numerous variations of the details may be made without departing from the invention as described in the appended claims.

We claim:

1. A method of identifying at least one favorable attachment site for a polymeric moiety on a target protein comprising:
   a) inputting a set of coordinates into a computer for said target protein;
   b) inputting a set of coordinates for said polymeric moiety;
   c) selecting a criteria for said favorable attachment site based upon at least one desired characteristic,
   d) using a simulation module comprising the steps of:
      i) computationally attaching conformers of said polymeric moiety to a plurality of amino acids in said target protein; and
      ii) disallowing conformers at each of said amino acids on the basis of a distance cutoff;
   e) selecting based upon said criteria one of said amino acids for attachment of said polymeric moiety; and
   f) physically making and screening for said at least one desired characteristic at least one target protein with a polymeric moiety attached at said favorable attachment site amino acid position.

2. The method according to claim 1, wherein said method further comprises identifying a set of polymer sizes for attachment to said favorable attachment site.

3. The method according to claim 1, wherein the amino acid at said position is a non-naturally occurring amino acid.

4. The method according to claim 3, wherein said non-naturally occurring amino acid is p-acetyl-L-phenylalanine.

5. The method according to claim 1, wherein said polymeric moiety for attachment is pharmaceutically acceptable.

6. The method according to claim 5, wherein said polymeric moiety for attachment is a polyethylene glycol (PEG).

7. The method according to claim 6, wherein said PEG is a PEG derivative.

8. The method according to claim 1, wherein said polymeric moiety for attachment has a range of about 1000 daltons to about 100,000 daltons.

9. The method according to claim 1, wherein said polymeric moiety for attachment is branched.

10. The method according to claim 1, wherein said polymeric moiety for attachment is unbranched.

11. The method according to claim 1, wherein said polymeric moiety for attachment is labile.

12. The method according to claim 1, wherein said protein is a therapeutic protein.

13. The method according to claim 1, wherein said protein is selected from the group consisting of a human erythropoeitin (EPO), a human tumor necrosis factor (TNF), a human growth hormone (hGH), a human interferon (IFN), a human granulocyte colony stimulating factor (G-CSF) and bone morphogenic protein-7 (BMP7).

14. The method according to claim 1, wherein said simulation module includes Monte Carlo (MC) simulations, Molecular Dynamics (MD) simulations or combinations thereof.

15. The method according to claim 1, further comprising substituting at least one amino acid at said favorable attachment site with a cysteine residue.

16. The method according to claim 1, further comprising substituting at least one lysine or histidine residue of said protein with any other amino acid residue.

* * * * *